US012622757B2

(12) United States Patent (10) Patent No.: US 12,622,757 B2

Ke et al. (45) Date of Patent: May 12, 2026

(54) USER INTERFACE FOR THREE DIMENSIONAL IMAGING AND TREATMENT

(71) Applicant: PROCEPT BioRobotics Corporation, Redwood City, CA (US)

(72) Inventors: Qingxiang Ke, San Jose, CA (US); Peter Bentley, Reno, NV (US); Nishey Wanchoo, San Mateo, CA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 376 days.

(21) Appl. No.: 18/163,187

(22) Filed: Feb. 1, 2023

(65) Prior Publication Data

US 2024/0252255 A1 Aug. 1, 2024

(51) Int. Cl.
*A61B 34/00* (2016.01)
*A61B 34/10* (2016.01)
(Continued)

(52) U.S. Cl.
CPC .......... *A61B 34/25* (2016.02); *G06F 3/04815* (2013.01); *G06F 3/04845* (2013.01);
(Continued)

(58) Field of Classification Search
CPC .............. A61B 34/25; A61B 2034/104; A61B 2034/107; A61B 2090/367;
(Continued)

(56) References Cited

U.S. PATENT DOCUMENTS 8,152,816 B2 4/2012 Tuma
8,229,188 B2 7/2012 Rusko
(Continued)

FOREIGN PATENT DOCUMENTS

CN 211068801 U * 7/2020
CN 113633372 11/2021
(Continued)

OTHER PUBLICATIONS

International Search Report and Written Opinion for PCT/US2024/013449, 13 pages (Jun. 17, 2024).
(Continued)

*Primary Examiner* — Said Broome
*Assistant Examiner* — Denis Vasiliy Minko
(74) *Attorney, Agent, or Firm* — Knobbe, Martens, Olson & Bear, LLP

(57) ABSTRACT

A user interface presents a 3D view of the tissue and treatment plan. The 3D view comprises a plurality of transverse images arranged along a one or more longitudinal images. The user adjusts the treatment profile with input to the user interface, and an updated treatment profile is shown on the other views. The user to one or more of zoom, pan, or rotate the 3D view with the treatment profile overlaid on the 3D view, and the treatment profile moves with the 3D view to maintain registration with the 3D view. In some embodiments, a 3D treatment plan is generated in accordance with a plurality of angles between a treatment probe and the one or more tissue structures. An AI algorithm can be used to identify tissue structures and plan the treatment angles and energy delivery in accordance with the tissue structures, which can provide a more customized treatment.

19 Claims, 16 Drawing Sheets

(51) Int. Cl.

| | | |
|---|---|---|
| *A61B 90/00* | (2016.01) |
| *G06F 3/04815* | (2022.01) |
| *G06F 3/04845* | (2022.01) |
| *G06F 3/0485* | (2022.01) |
| *G06T 13/20* | (2011.01) |
| *G06T 19/20* | (2011.01) |

(52) U.S. Cl.
CPC .............. *G06T 13/20* (2013.01); *G06T 19/20* (2013.01); *A61B 2034/104* (2016.02); *A61B 2034/107* (2016.02); *A61B 2090/367* (2016.02); *G06F 3/0485* (2013.01); *G06F 2203/04806* (2013.01); *G06T 2200/24* (2013.01); *G06T 2210/41* (2013.01); *G06T 2210/62* (2013.01); *G06T 2219/2004* (2013.01); *G06T 2219/2016* (2013.01)

(58) Field of Classification Search
CPC .............. A61B 2034/105; A61B 34/10; G06F 3/04815; G06F 3/04845; G06F 3/0485; G06F 2203/04806; G06T 13/20; G06T 19/20; G06T 2200/24; G06T 2210/41; G06T 2210/62; G06T 2219/2004; G06T 2219/2016
See application file for complete search history.

(56) References Cited

U.S. PATENT DOCUMENTS

| | | | |
|---|---|---|---|
| 9,144,461 | B2 | 9/2015 | Kruecker |
| 9,277,969 | B2 | 3/2016 | Brannan |
| 10,226,298 | B2 | 3/2019 | Ourselin |
| 10,423,757 | B2 | 9/2019 | Kruecker |
| 10,448,956 | B2 | 10/2019 | Gordon |
| 11,278,451 | B2 | 3/2022 | Andrews |
| 2008/0027420 | A1 | 1/2008 | Wang |
| 2011/0299750 | A1 | 12/2011 | Cool |
| 2012/0130241 | A1 | 5/2012 | Wang |
| 2016/0256225 | A1 | 9/2016 | Crawford |
| 2016/0332005 | A1 | 11/2016 | Fedewa |
| 2017/0273797 | A1 | 9/2017 | Gordon |
| 2017/0333137 | A1 | 11/2017 | Roessler |
| 2018/0028261 | A1 | 2/2018 | Chen |
| 2018/0318011 | A1 | 11/2018 | Leibinger |
| 2019/0000319 | A1 | 1/2019 | Mak |
| 2019/0064290 | A1 | 2/2019 | Bailey |
| 2019/0069962 | A1 | 3/2019 | Tabandeh |
| 2019/0201214 | A1 | 7/2019 | Miller |
| 2020/0360100 | A1 | 11/2020 | Mantri |
| 2020/0375622 | A1 | 12/2020 | Aljuri |
| 2021/0121251 | A1 | 4/2021 | Aljuri |
| 2022/0133284 | A1* | 5/2022 | Lampotang ........ A61B 10/0241 600/562 |
| 2022/0133331 | A1 | 5/2022 | Abbasi |
| 2022/0222812 | A1* | 7/2022 | Li .......................... G06N 3/045 |
| 2022/0241037 | A1 | 8/2022 | Crawford |
| 2022/0241981 | A1 | 8/2022 | Fredrickson |
| 2022/0338836 | A1* | 10/2022 | Doron .................... A61B 8/461 |
| 2023/0008419 | A1* | 1/2023 | Wilson .................. A61B 34/30 |
| 2024/0285346 | A1 | 8/2024 | Shi |
| 2024/0299003 | A1 | 9/2024 | Shi |

FOREIGN PATENT DOCUMENTS

| | | | | |
|---|---|---|---|---|
| CN | 113796952 | | 12/2021 | |
| CN | 113940753 | | 1/2022 | |
| CN | 113951935 | | 1/2022 | |
| CN | 106572827 | B * | 2/2022 | .......... A61B 1/2676 |
| CN | 114145781 | | 3/2022 | |
| CN | 114320879 | | 4/2022 | |
| CN | 114376610 | | 4/2022 | |
| CN | 114521939 | | 5/2022 | |
| CN | 216495529 | | 5/2022 | |
| CN | 216675776 | | 6/2022 | |
| CN | 216675785 | | 6/2022 | |
| CN | 217338655 | | 9/2022 | |
| CN | 115607282 | | 1/2023 | |
| CN | 115634042 | | 1/2023 | |
| CN | 115955052 | | 4/2023 | |
| EP | 1486900 | | 12/2004 | |
| KR | 101869826 | | 6/2018 | |
| WO | 2008083407 | | 7/2008 | |
| WO | 2009111736 | | 9/2009 | |
| WO | 2011097505 | | 8/2011 | |
| WO | 2011097505 | A1 | 8/2011 | |
| WO | WO-2012082804 | A2 * | 6/2012 | .......... G06T 7/0012 |
| WO | 2013053614 | | 4/2013 | |
| WO | 2013130895 | | 9/2013 | |
| WO | 2013130895 | A1 | 9/2013 | |
| WO | 2014127242 | | 8/2014 | |
| WO | 2014127242 | A2 | 8/2014 | |
| WO | 2014165703 | | 10/2014 | |
| WO | 2014165703 | A1 | 10/2014 | |
| WO | 2015035249 | | 3/2015 | |
| WO | 2015035249 | A2 | 3/2015 | |
| WO | 2015200538 | | 12/2015 | |
| WO | 2015200538 | A1 | 12/2015 | |
| WO | 2016004071 | | 1/2016 | |
| WO | 2016004071 | A1 | 1/2016 | |
| WO | 2016037132 | | 3/2016 | |
| WO | 2016037132 | A1 | 3/2016 | |
| WO | 2016037137 | | 3/2016 | |
| WO | 2016037137 | A1 | 3/2016 | |
| WO | 2017161331 | | 9/2017 | |
| WO | 2017161331 | A1 | 9/2017 | |
| WO | 2019032986 | | 2/2019 | |
| WO | 2019137665 | | 7/2019 | |
| WO | WO-2019145343 | A1 * | 8/2019 | .............. A61B 8/52 |
| WO | 2019246580 | | 12/2019 | |
| WO | 2020180724 | | 9/2020 | |
| WO | 2020181278 | | 9/2020 | |
| WO | 2020181280 | | 9/2020 | |
| WO | 2020181281 | | 9/2020 | |
| WO | 2020181290 | | 9/2020 | |
| WO | WO-2020186198 | A1 * | 9/2020 | ............. A61B 34/20 |
| WO | WO-2021003304 | A1 * | 1/2021 | ........ A61F 9/00781 |
| WO | 2021096741 | | 5/2021 | |
| WO | WO-2021210642 | A1 * | 10/2021 | .......... G01N 33/487 |
| WO | 2021262565 | | 12/2021 | |
| WO | 2021263276 | | 12/2021 | |
| WO | 2022006248 | | 1/2022 | |
| WO | 2022011177 | | 1/2022 | |
| WO | 2022226103 | | 10/2022 | |
| WO | 2023066148 | | 4/2023 | |
| WO | 2023072146 | | 5/2023 | |
| WO | 2023083352 | | 5/2023 | |
| WO | 2023088305 | | 5/2023 | |
| WO | 2023159096 | | 8/2023 | |
| WO | 2023159101 | | 8/2023 | |
| WO | 2023179756 | | 9/2023 | |
| WO | 2023207917 | | 11/2023 | |
| WO | 2024114841 | | 6/2024 | |
| WO | 2024140703 | | 7/2024 | |

OTHER PUBLICATIONS

Garnica-Garza, HM. Directional scatter imaging for the stereoscopic tracking of fiducial markers in a single kV exposure. Med Phys. Feb. 2018;45(2):703-713. doi: 10.1002/mp.12712. Epub Dec. 21, 2017. PMID: 29206280.

Košťák M, Slabý A. Designing a Simple Fiducial Marker for Localization in Spatial Scenes Using Neural Networks. Sensors (Basel). Aug. 10, 2021;21(16):5407. doi: 10.3390/s21165407. PMID: 34450848; PMCID: PMC8400176.

Stathakis, Alexandros, "Vision-Based Localization using Reliable Fiducial Markers," retrieved from https://citeseerx.ist.psu.edu/viewdoc/download?doi=10.1.1.895.3616&rep=rep1&type=pdf (Dec. 2011).

(56)            References Cited

OTHER PUBLICATIONS

International Search Report and Written Opinion issued in International Patent Application No. PCT/US2023/77776, dated Apr. 30, 2024, in 14 pages.

\* cited by examiner

Perspective view

Sagittal view

Superior view

Superior view

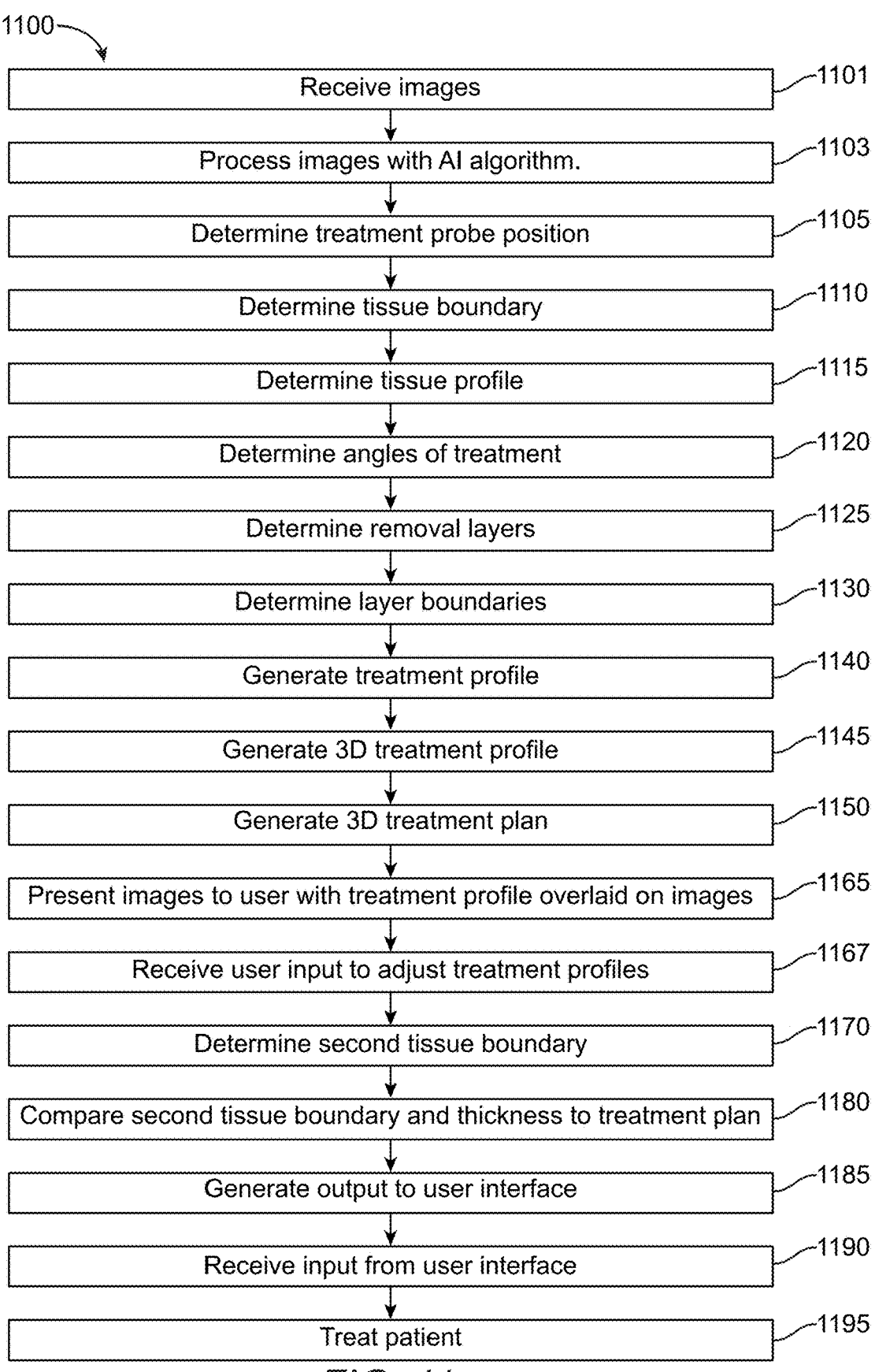

1100

Receive images — 1101

Process images with AI algorithm. — 1103

Determine treatment probe position — 1105

Determine tissue boundary — 1110

Determine tissue profile — 1115

Determine angles of treatment — 1120

Determine removal layers — 1125

Determine layer boundaries — 1130

Generate treatment profile — 1140

Generate 3D treatment profile — 1145

Generate 3D treatment plan — 1150

Present images to user with treatment profile overlaid on images — 1165

Receive user input to adjust treatment profiles — 1167

Determine second tissue boundary — 1170

Compare second tissue boundary and thickness to treatment plan — 1180

Generate output to user interface — 1185

Receive input from user interface — 1190

Treat patient — 1195

FIG. 11

USER INTERFACE FOR THREE DIMENSIONAL IMAGING AND TREATMENT

RELATED APPLICATIONS

None.

BACKGROUND

Prior approaches to tissue planning and treatment with an energy source can be less than ideal in at least some respects. In at least some instances, the energy directed toward the treated tissue may not be appropriate in at least some respects and may over or under treat the targeted tissue. Work in relation to the present disclosure suggests that an energy source may not be accurately directed to the targeted tissue in at least some instances. Also, some types of surgery treat tissue near a delicate untargeted tissue, the prior approaches may result in greater amounts of energy being delivered to the untargeted tissue in at least some instances.

Although image guided treatment in which a user can review treatment profiles overlaid on patient images prior to treatment has been proposed, work in relation to the present disclosure suggests that the prior user interfaces may be somewhat more complex or provide gaps in the treatment regions that are reviewed in at least some instances. It would be helpful to provide an improved user interface that allows a user to quickly review the planned treatment with appropriate images. Also, at least some prior approaches to imaging tissue with probes can be somewhat more complex than would be ideal and can be somewhat more sensitive to alignment between a treatment probe and an imaging probe than would be ideal in at least some instances.

Although the recognition of tissue with artificial intelligence has been proposed, at least some of these prior approaches are not well suited for combination with surgical treatment planning. For at least some types of surgery, it would be helpful to have an improved user interface that allows a user to review and verify a treatment plan prior to treating the patient.

In light of the above, there is a need for improved tissue treatment with energy and treatment planning that ameliorate at least some of the aforementioned limitations of the prior approaches.

SUMMARY

In some embodiments, a user interface is configured for a user to review a treatment prior to treating the patient, which can facilitate treatment planning. In some embodiments, a user interface is configured to provide a plurality of images which have been rotated with respect to an axis of treatment, such as an axis of an energy source on a probe, which facilitate treatment planning. In some embodiments, a user interface is configured to a present a 3D view of the tissue and treatment plan such as a treatment profile. In some embodiments, the 3D view comprises a plurality of transverse images arranged along one or more longitudinal images, which can give the user an improved perspective of the treatment during treatment planning. In some embodiments, the one or more longitudinal images correspond to a longitudinal axis of a treatment probe. Alternatively or in combination, the one or more longitudinal images may correspond to a longitudinal axis of an imaging probe that acquires the images. In some embodiments, the one or more longitudinal images comprise images that have been rotated such that at least one of the one or more longitudinal images extends substantially along an elongate axis of a treatment probe, and the plurality of transverse images may comprise images that have been rotated in accordance with the rotation of the one or more longitudinal images.

In some embodiments, the user interface is configured for the user to select one or more views in addition to the 3D view, such a plurality of transverse views and one or more longitudinal views. The one or more longitudinal views may comprise one or more sagittal images such as one or more sagittal or parasagittal images. In some embodiments, the user interface is configured for the user to adjust the treatment profile with input to the user interface, and an updated treatment profile is shown on the other views. In some embodiments, the user interface is configured for the user to one or more of zoom, pan, or rotate the 3D view with the treatment profile overlaid on the 3D view, and the treatment profile moves with the 3D view to maintain registration with the 3D view while the 3D view is one or more of zoomed, panned or rotated. This approach can allow the user to obtain a better understanding of the treatment and locations of tissue structures with respect to planned treatment, such as a planned treatment profile.

In some embodiments, a 3D treatment plan is generated from a plurality of images, such as one or more longitudinal images and a plurality of transverse images. In some embodiments, the 3D treatment plan is generated in accordance with a plurality of angles between a treatment probe and the one or more tissue structures. While the treatment plan can be generated in many ways, in some embodiments an AI algorithm is used to identify tissue structures and plan the treatment angles and energy delivery in accordance with the tissue structures, which can provide a more customized treatment. In some embodiments, the AI generated treatment plan is provided to the user on a user interface, such that the user can verify the AI generated treatment parameters. While this verification can be performed in many ways, in some embodiments the AI generated treatment plan is presented to the user with a plurality of views, which can allow the user to verify the AI generated treatment plan. In some embodiments, the user interface is configured for the user to select a plurality of views and to adjust the AI generated treatment plan.

In some embodiments, a method of planning a treatment comprises receiving a plurality of transverse images and one or more longitudinal images and generating an arrangement of the plurality of transverse images along the one or more longitudinal images in a three-dimensional (3D) view. The one or more longitudinal images may comprise one or more sagittal or parasagittal images. The three dimensional view may comprise the plurality of transverse images at a plurality corresponding locations along the one or more longitudinal images, such as one or more sagittal or parasagittal images. A representation of a three dimensional (3D) treatment profile is overlaid on the 3D view of the plurality of transverse images and the one or more longitudinal images, and the 3D view with the representation overlaid on the one or more longitudinal images and one or more of the plurality of transverse images is shown on a display of a user interface.

In some embodiments, a method of generating a treatment plan comprises receiving a plurality of transverse images of a tissue to be treated. For each of the plurality of transverse images, a position of a treatment probe and a boundary of the tissue is determined, in which the boundary is used to define an area of the tissue to be treated.

In some embodiments, for each of the plurality of transverse images, a first boundary angle from the treatment probe to a first location along the boundary on a first side of the area is determined and a second boundary angle from the treatment probe to a second location along the boundary on a second side of the area is determined. The angles of the tissue boundary with respect to the treatment probe can be used to determine the angles of treatment. The angles of treatment may be determined in response to the angles of the boundary so as to provide one or more tissue margins near the edges of the treatment. Alternatively or in combination, the angles of treatment can be determined in response to a tissue penetration depth of an energy source and the thickness of the tissue at an angle to the energy source, so as to provide a depth margin. In some embodiments, the tissue margin comprises a safety margin to decrease interaction with other tissue near the tissue margin, such as a verumontanum of a prostate or a trigone region of the bladder.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

4

Figures 7A, 7B:
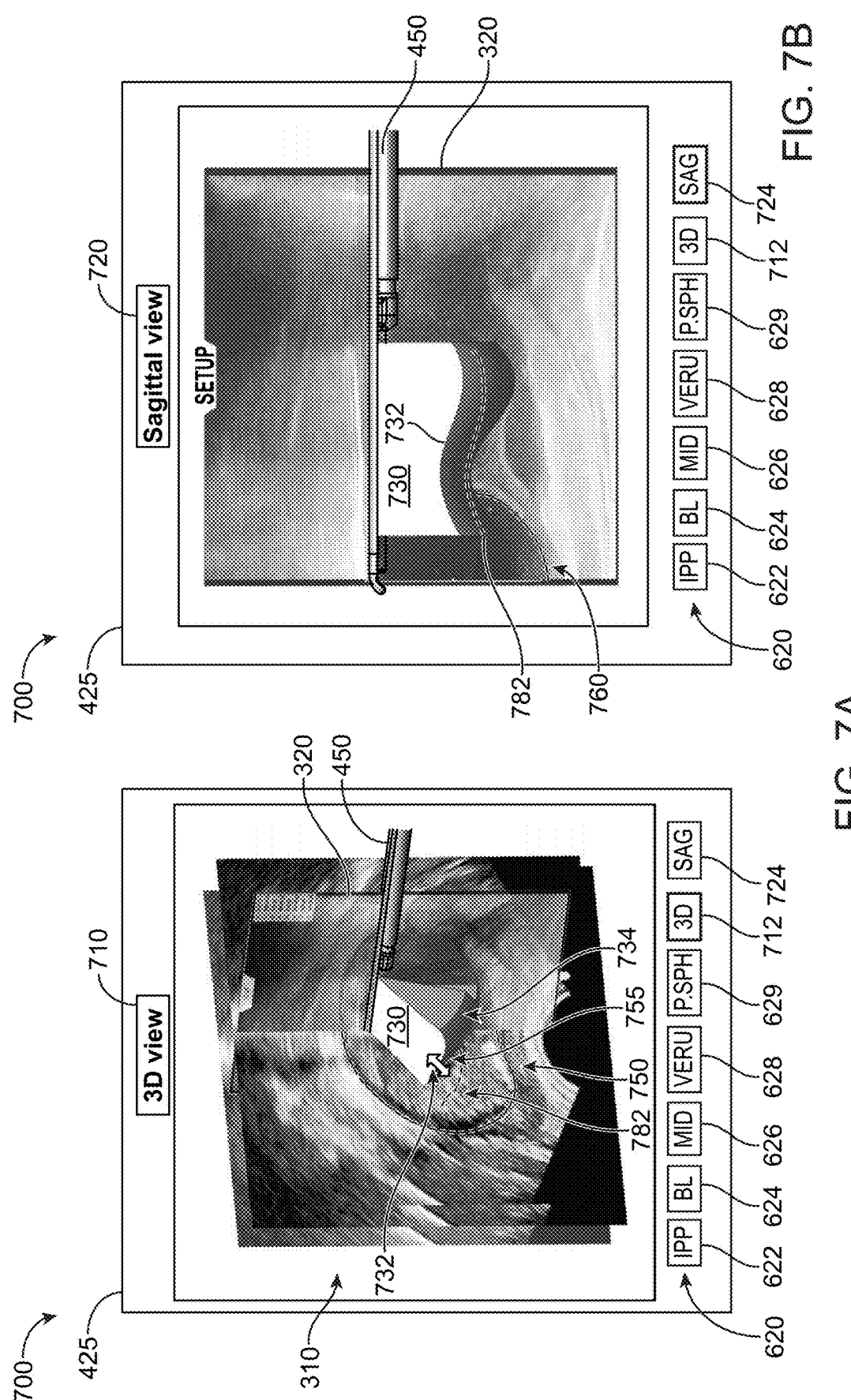
Figures 7C, 7D:
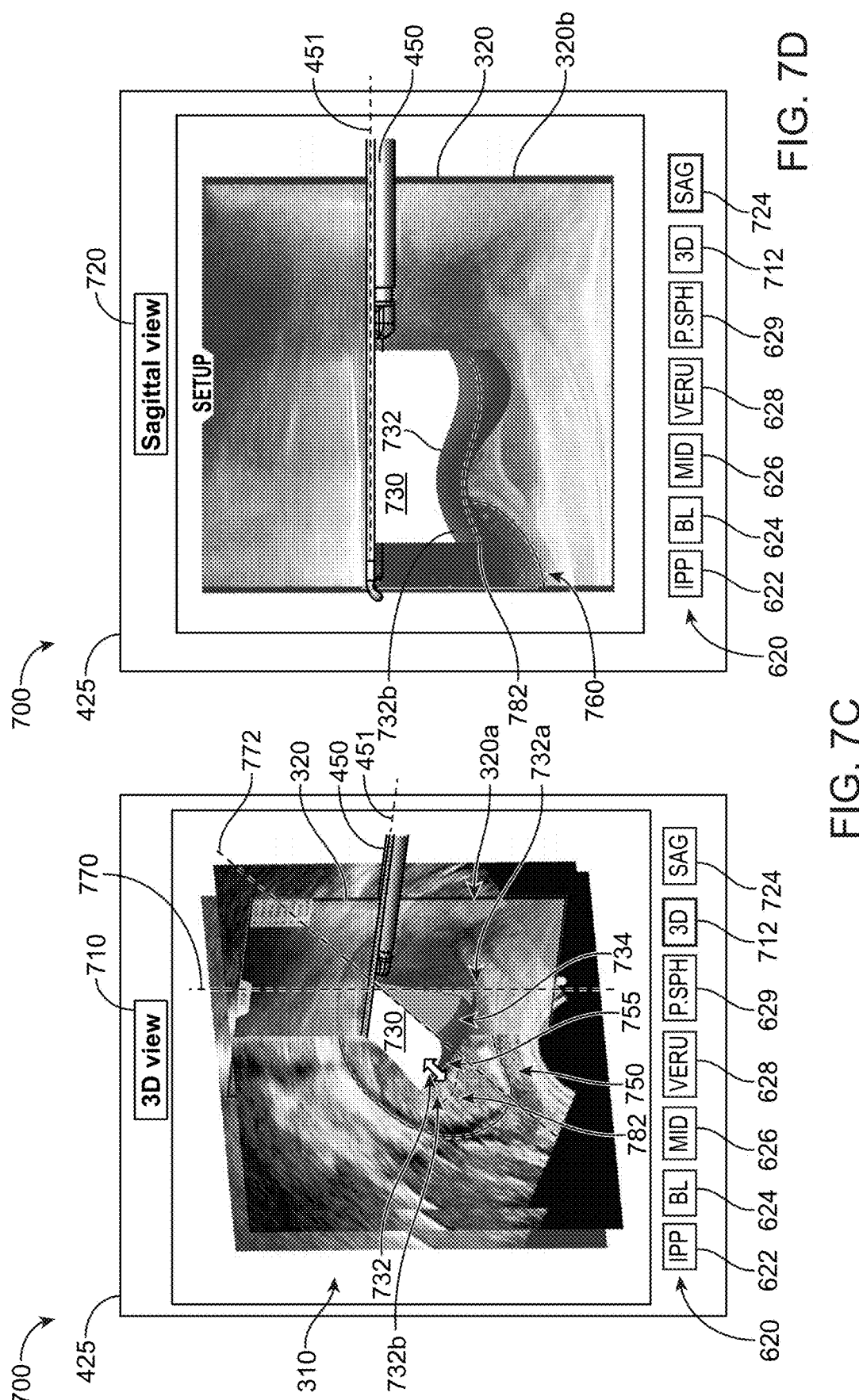
Figures 8A, 8B:
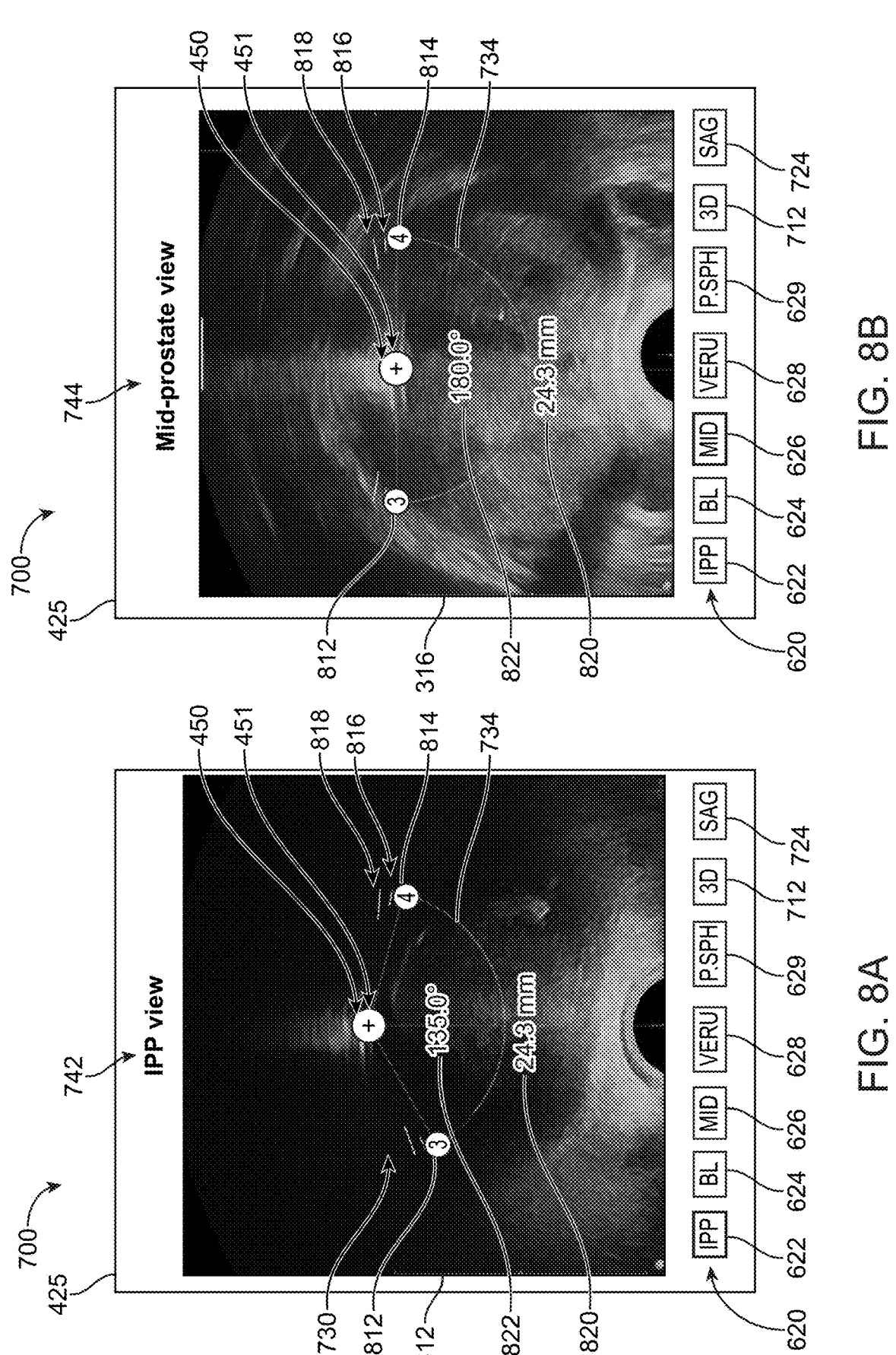
Figures 9A, 9B:
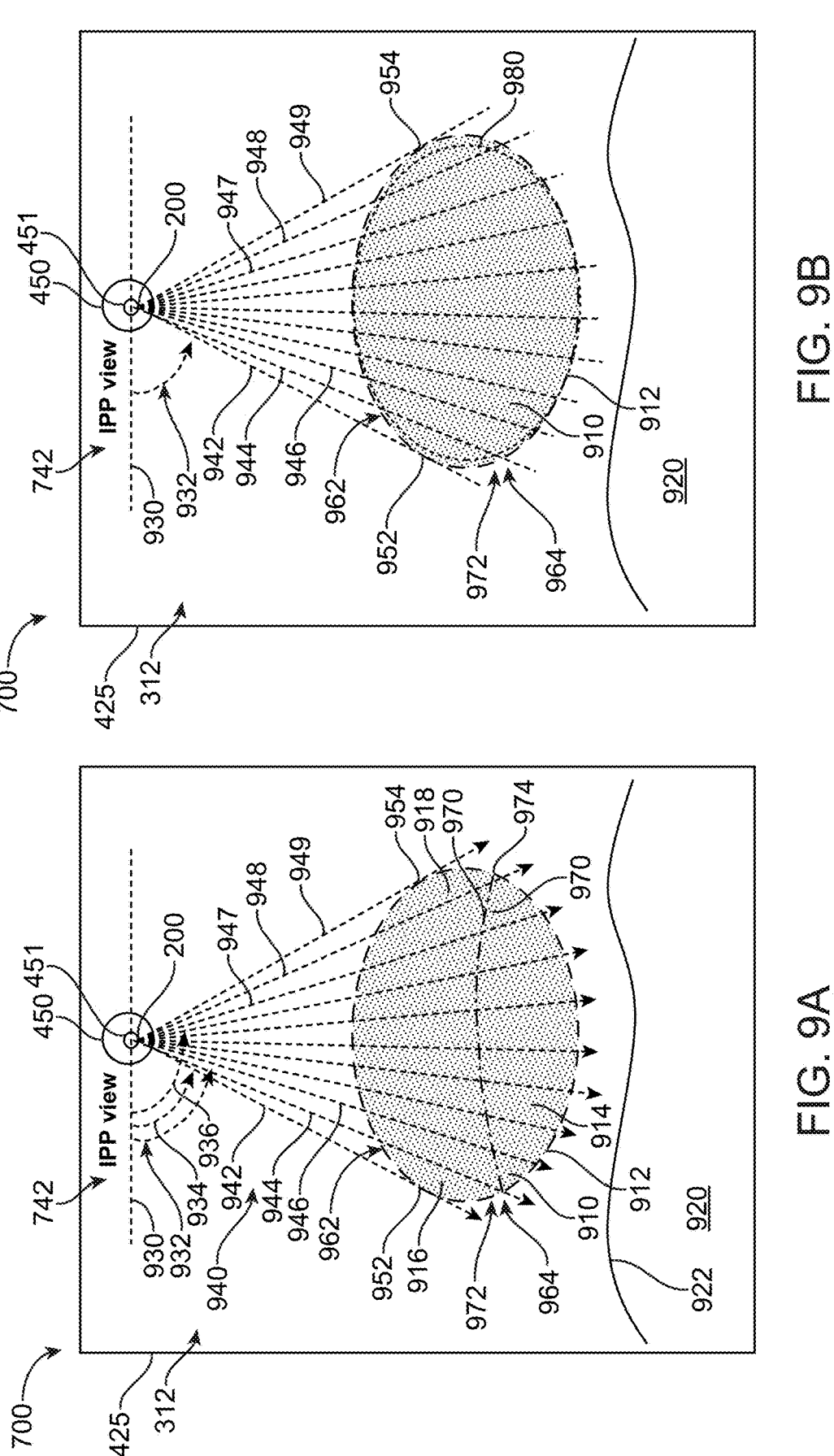
Figures 9C, 9D:
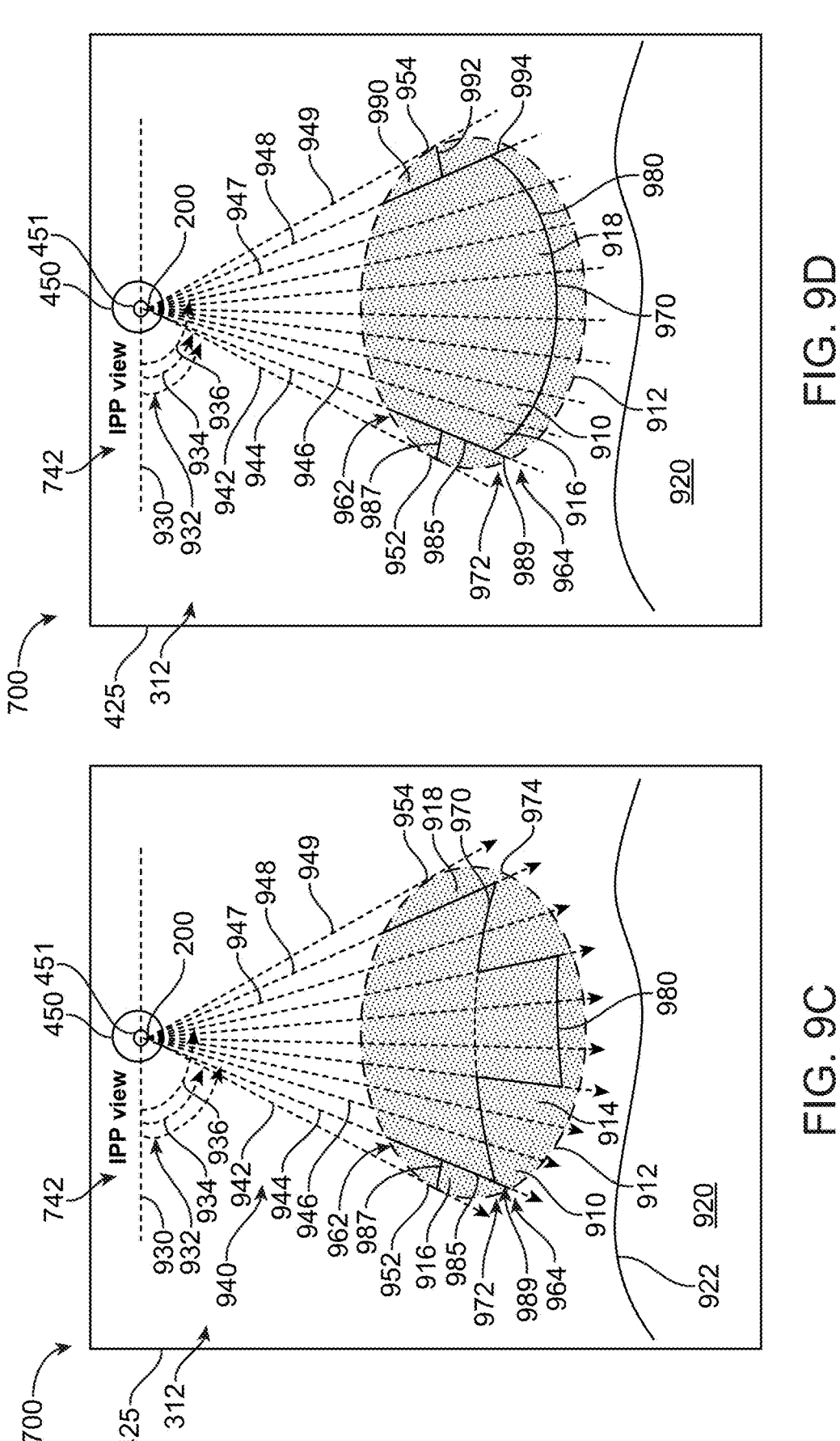
Figure 10:
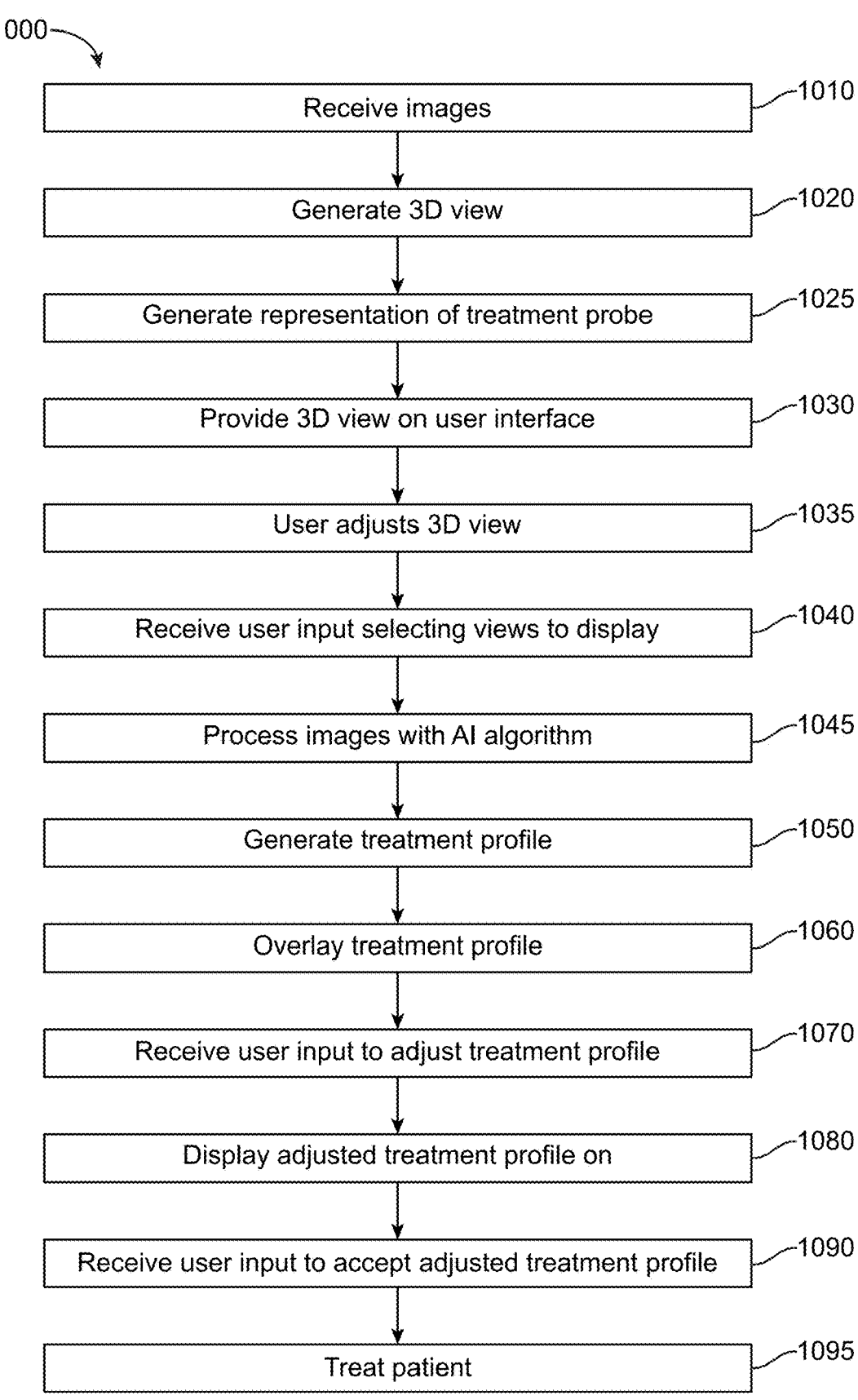
Figure 12:
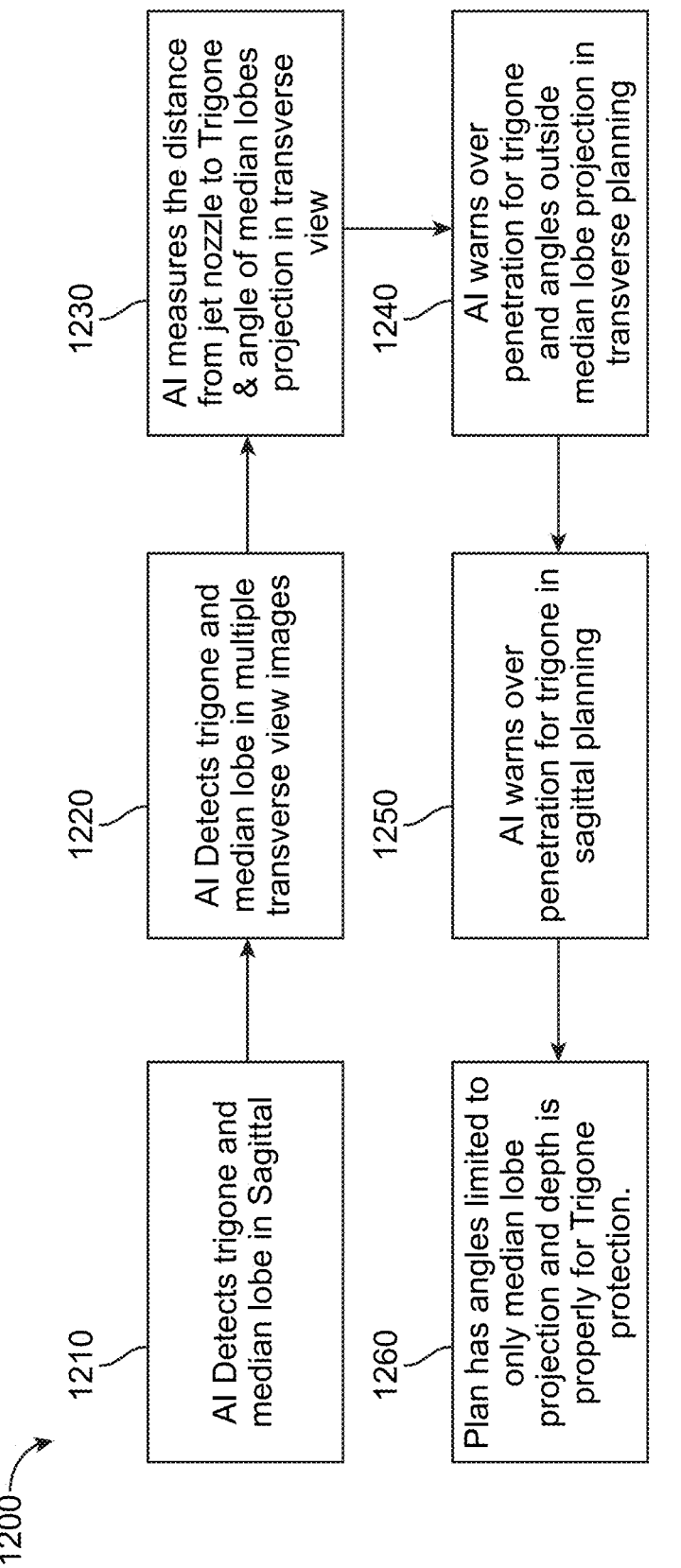
Figure 13:
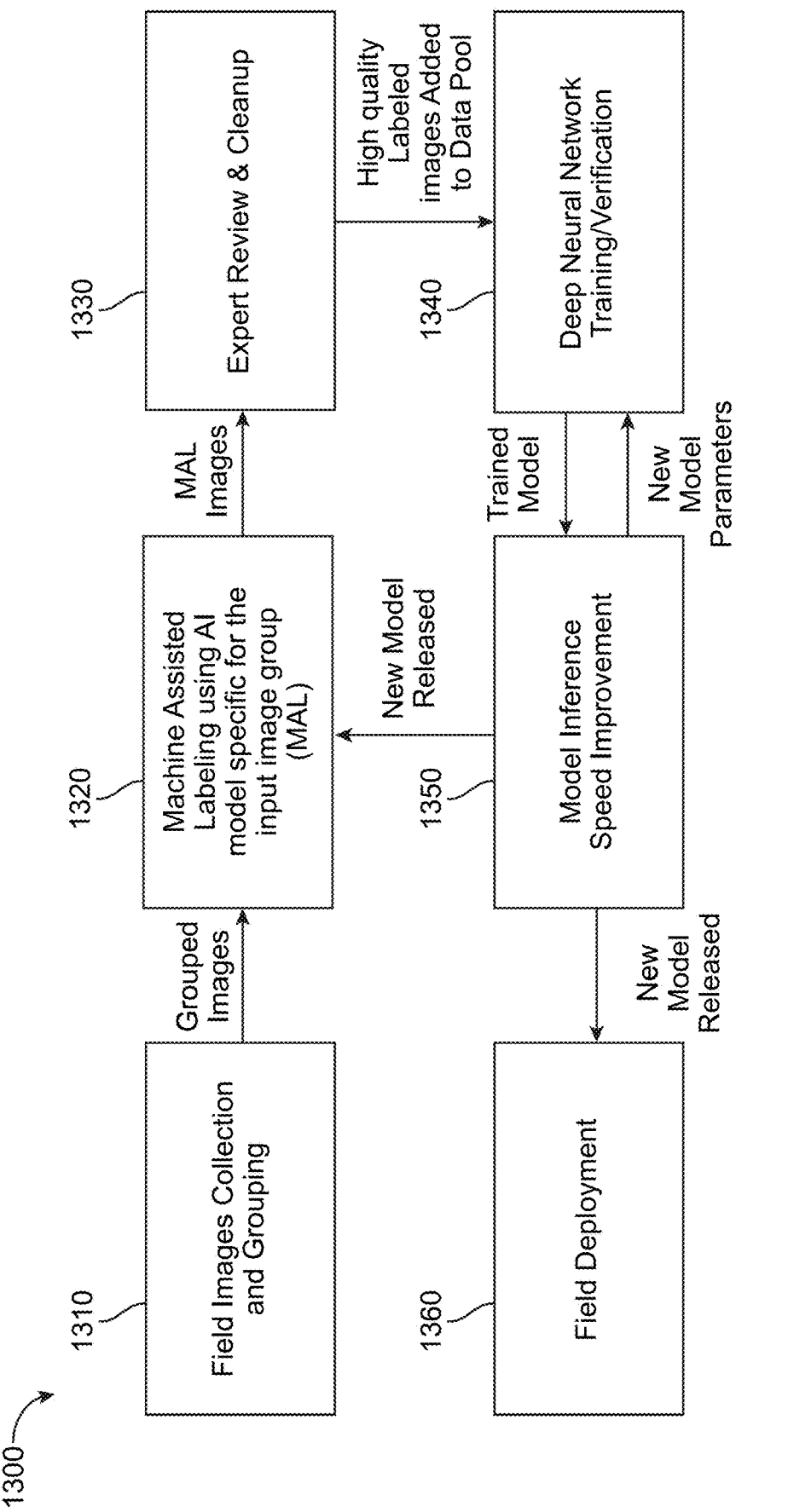
Figure 14:
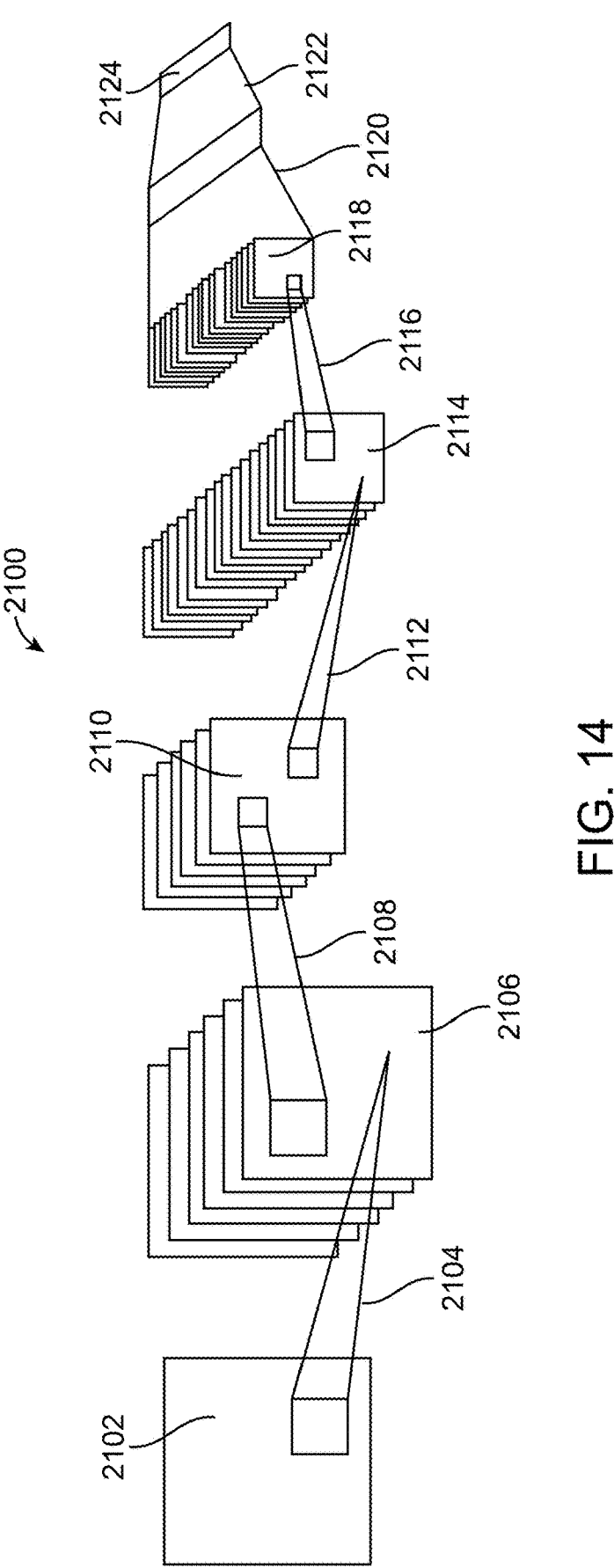

FIG. 7A shows a user interface with a three dimensional view for three dimensional treatment planning, in accordance with some embodiments;

FIG. 7B shows a longitudinal image such as a sagittal image for three dimensional treatment planning, in accordance with some embodiments;

FIGS. 7C and 7D show a plurality of rotational angles relative to the treatment probe that can be used to generate a plurality of longitudinal images, in accordance with some embodiments;

FIG. 8A shows a first transverse view for three dimensional treatment planning at a first depth of a three dimensional treatment profile, in accordance with some embodiments;

FIG. 8B shows a second transverse view for three dimensional treatment planning at a second depth, in accordance with some embodiments FIG. 9A shows a probe and rotational angles of an energy source on the probe to direct the energy source toward tissue to treat the tissue to different depths, in accordance with some embodiments;

FIG. 9B shows a probe and rotational angles and a treatment profile overlaid on an images of tissue, in accordance with some embodiments;

FIGS. 9C and 9D show treatment plans with one or more tissue margins, in accordance with some embodiments;

FIG. 10 shows a method of planning a three-dimensional treatment (3D) with a user interface, in accordance with some embodiments;

FIG. 11 shows a method of planning a 3D treatment with automated tissue recognition, in accordance with some embodiments;

FIG. 12 shows a method of treating a first tissue and decreasing exposure to a second tissue with automated tissue recognition, in accordance with some embodiments;

FIG. 13 shows a method of training an artificial intelligence (AI) algorithm, in accordance with some embodiments; and FIG. 14 shows a two-dimensional convolutional neural network, in accordance with some embodiments.

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed systems and methods are well suited for use with many probes and diagnostic and surgical procedures. Although reference is made to a treatment probe comprising an energy source for prostate surgery and a transrectal ultrasound ("TRUS") probe, the present disclosure is well suited for use with many types of probes inserted into many types of tissues, organs, cavities and lumens, such as brain, heart, lung, intestinal, eye, skin, kidney, liver, pancreas, stomach, uterus, ovaries, testicles, bladder, ear, nose, mouth, tumors, cancers, soft tissues such as bone marrow, adipose tissue, muscle, glandular and mucosal tissue, spinal and nerve tissue, cartilage, hard biological tissues such as teeth, bone, and lumens such as vascular lumens, nasal lumens and cavities, sinuses, colon, urethral lumens, gastric lumens, airways, esophageal lumens, trans esophageal, intestinal lumens, anal lumens, vaginal lumens, trans abdominal, abdominal cavities, throat, airways, lung passages, and surgery such as kidney surgery, ureter surgery, kidney stones, prostate surgery, tumor surgery, cancer surgery, brain surgery, heart surgery, eye surgery, conjunctival surgery, liver surgery, gall bladder surgery, bladder surgery, spinal surgery, orthopedic surgery, arthroscopic surgery, liposuction, colonoscopy, intubation, minimally invasive incisions, minimally invasive surgery, and others.

The presently disclosed systems and methods are well suited for combination with prior probes such as imaging probes and treatment probes. Examples of such probes include laser treatment probes, water jet probes, RF treatment probes, radiation therapy probes, ultrasound treatment probes, phaco emulsification probes, imaging probes, endoscopic probes, resectoscope probes, ultrasound imaging probes, A-scan ultrasound probes, B-scan ultrasound probes, 3D ultrasound probes, Doppler ultrasound probes, transrectal ultrasound probes, transvaginal ultrasound probes, longitudinal plane ultrasound imaging probes, sagittal plane ultrasound imaging probes, transverse plane ultrasound imaging probes, and transverse and longitudinal plane (e.g. sagittal plane) ultrasound imaging probes, for example.

The presently disclosed systems, methods and apparatuses are well suited for combination with many prior surgical procedures, such as water jet enucleation of the prostate, transurethral resection of the prostate (TURP), holmium laser enucleation of the prostate (HOLEP), prostate brachytherapy and with surgical robotics systems and automated surgical procedures. The following patent applications describe examples of systems, methods, probes and procedures suitable for incorporation in accordance with the present disclosure: PCT/US2013/028441, filed Feb. 28, 2013, entitled "AUTOMATED IMAGE-GUIDED TISSUE RESECTION AND TREATMENT, published as WO 2013/130895; PCT/US2014/054412, filed Sep. 5, 2014, entitled "AUTOMATED IMAGE-GUIDED TISSUE RESECTION AND TREATMENT", published as WO 2015/035249; PCT/US2015/048695, filed Sep. 5, 2015, entitled "PHYSICIAN CONTROLLED TISSUE RESECTION INTEGRATED WITH TREATMENT MAPPING OF TARGET ORGAN IMAGES", published as WO2016037137; PCT/US2019/038574, filed Jun. 21, 2019, entitled "ARTIFICIAL INTELLIGENCE FOR ROBOTIC SURGERY", published as WO2019246580A1 on Dec. 26, 2019; PCT/US2020/021756, filed Mar. 9, 2020, entitled "ROBOTIC ARMS AND METHODS FOR TISSUE RESECTION AND IMAGING", published as WO/2020/181290; PCT/US2020/058884, filed on Nov. 4, 2020, entitled "SURGICAL PROBES FOR TISSUE RESECTION WITH ROBOTIC ARMS", published as WO/2021/096741; PCT/US2021/070760, filed on Jun. 23, 2021, entitled "INTEGRATION OF ROBOTIC ARMS WITH SURGICAL PROBES", published as WO/2021/263276; PCT/US2021/038175, filed on Jun. 21, 2021, entitled "SYSTEMS AND METHODS FOR DEFINING AND MODIFYING RANGE OF MOTION OF PROBE USED IN PATIENT TREATMENT", published as WO/2021/262565; and PCT/US2022/025617, filed on Apr. 20, 2022, entitled "SURGICAL PROBE WITH INDEPENDENT ENERGY SOURCES", published as WO/2022/226103 on Oct. 27, 2022; the entire disclosures of which are incorporated herein by reference.

In some embodiments, improved positional accuracy is provided for placement of an energy source and imaging probe. The energy source may comprise any suitable energy source, such as an electrode, a loop electrode, laser source, mechanical sheer, a mechanical energy source, a radiation energy source, a thermal energy source, a vibrational energy source, an ultrasound probe, cavitating ultrasound probe, a water jet, a variable pressure water jet, a pressure controlled water jet, a flow rate controlled water jet, a fluctuating pressure water jet, a fixed pressure water jet, plasma, steam, a morcellator, a trans urethral needle, photo ablation, water jet evacuation. The energy source can be combined with other treatments and compounds, such as compounds for treatment, hemostasis, photochemical treatment, or contrast agents for imaging. The imaging probe may comprise any suitable probe, such as endoscopic probes, resectoscope probes, ultrasound imaging probes, A-scan ultrasound probes, B-scan ultrasound probes, Doppler ultrasound probes, transrectal ultrasound probes, transvaginal ultrasound probes, longitudinal plane (e.g. sagittal plane) ultrasound imaging probes, transverse plane ultrasound imaging probes, and transverse and longitudinal (e.g. sagittal) plane ultrasound imaging probes, for example.

The probes comprising the energy source and the imaging probes can be configured in many ways and each may comprise one or more fiducials for determining a position and orientation of a respective probe.

Although the present disclosure refers to treatment planning with a probe inserted into the patient, the presently disclosed systems and methods are well suited for pre-treatment planning. In some embodiments, the treatment planning is performed without a probe inserted into the patient, for example with images obtained prior to one or more of the treatment probe or the image probe being inserted into the patient.

Although the present disclosure refers to an imaging probe that is separated from the treatment probe, the presently disclosed methods and apparatus are well suited for use with a treatment probe that comprises an imaging probe. In some embodiments the imaging probe is located on the treatment probe, for example. Examples of an imaging device such as an imaging array located on a rotating and translating treatment probe are described in PCT/US2013/028441, filed Feb. 28, 2013, entitled "AUTOMATED IMAGE-GUIDED TISSUE RESECTION AND TREATMENT, published as WO 2013/130895, the entire disclosure of which has been incorporated herein by reference.

Figure 1:
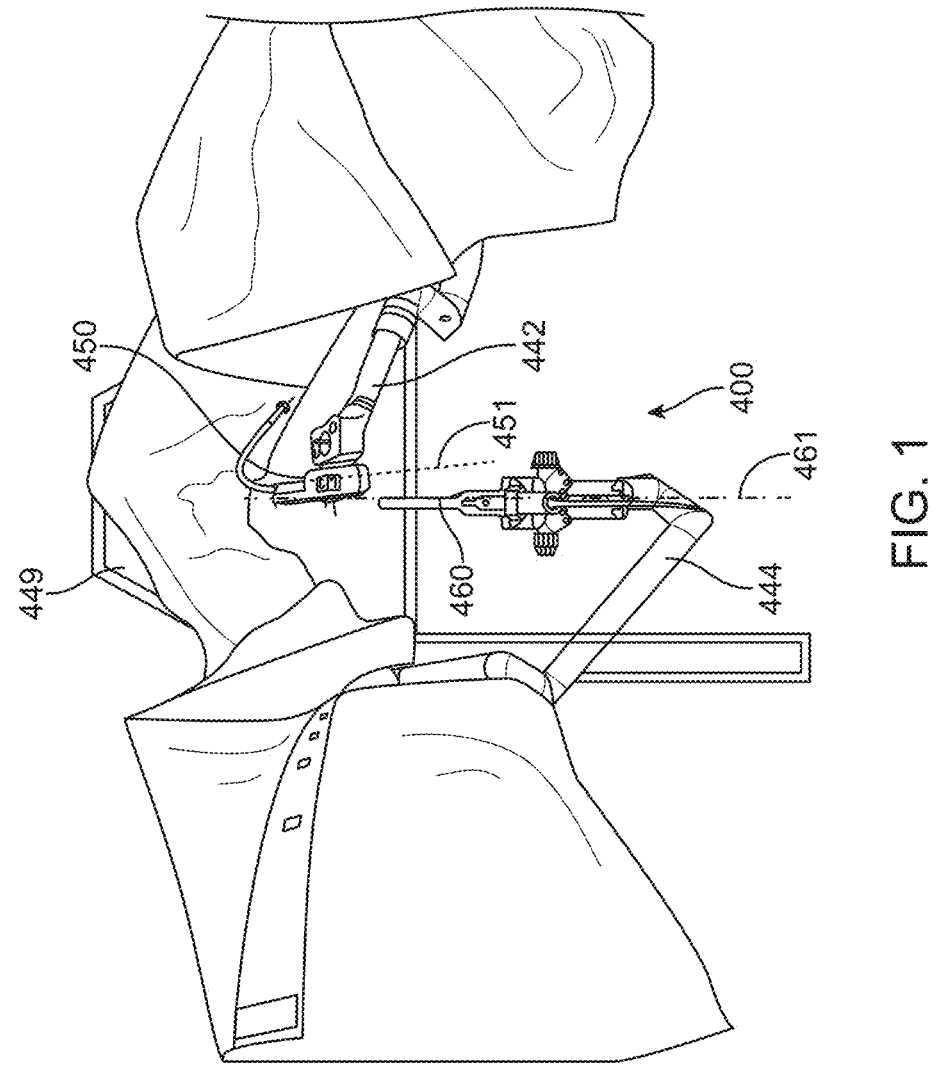
FIG. 1 shows a front view of a system for performing tissue resection in a patient, in accordance with some embodiments.

FIG. 1 shows an exemplary embodiment of a system 400 for performing treatment of a patient. The system 400 may comprise a treatment probe 450 as described herein and an imaging probe 460 as described herein. The treatment probe 450 may be coupled to a first arm 442, and the imaging probe 460 coupled to a second am 444. One or both of the first arm 442 and the second arm 444 may comprise robotic arms whose movements may be controlled by one or more computing devices operably coupled with the arms. The treatment probe 450 may comprise a device for removing target tissue from a target site within a patient. The treatment probe 450 may be configured to deliver energy from the treatment probe 450 to the target tissue sufficient for removing the target tissue, and the energy from the energy source may comprise any suitable energy as described herein. For example, the treatment probe 450 may comprise an electro-surgical ablation device, a laser ablation device, a transurethral needle ablation device, a water jet ablation device, a steam ablation device, a high-intensity focused ultrasound (HIFU) device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
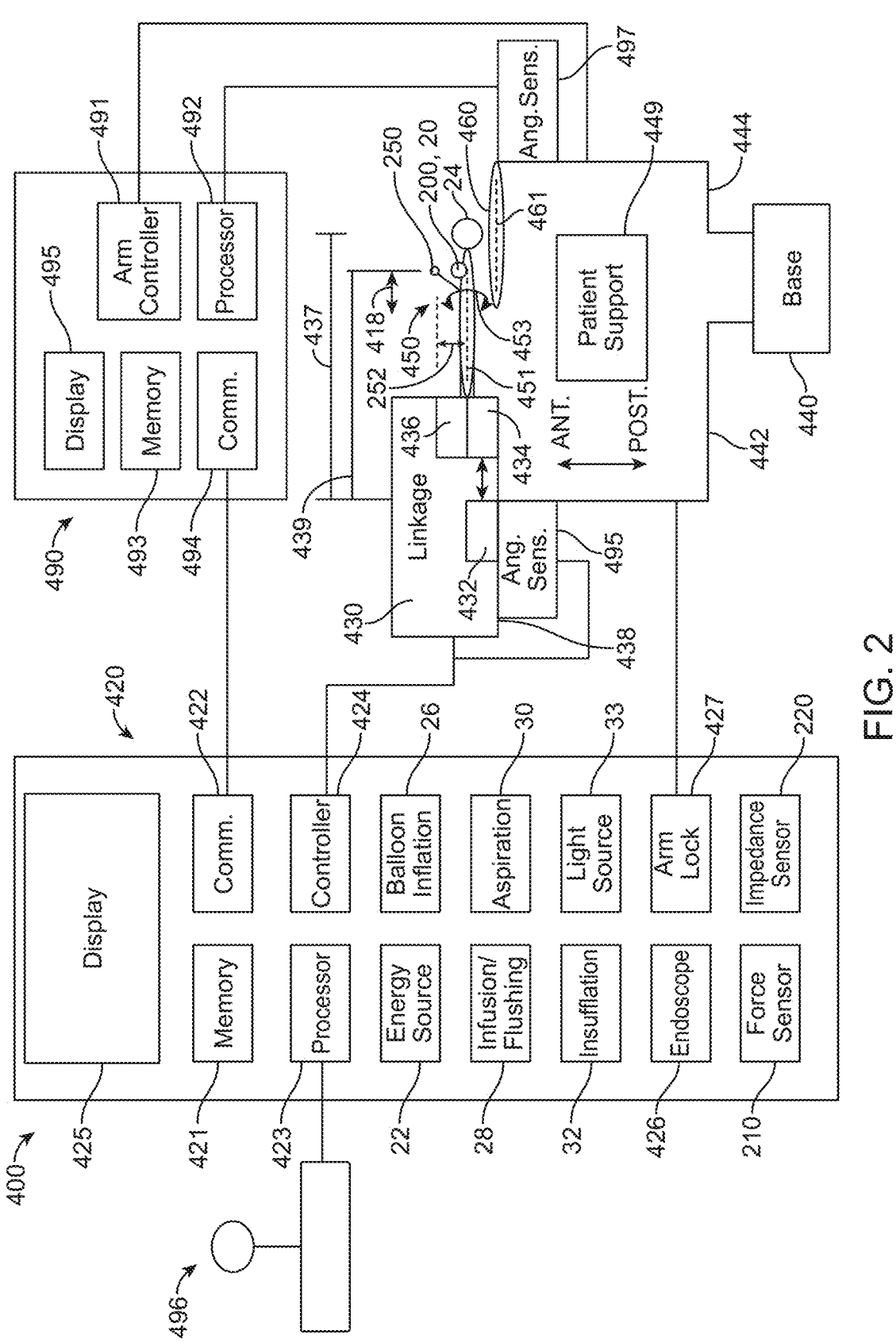
FIG. 2 schematically illustrates a system for performing tissue resection in a patient, in accordance with some embodiments.

FIG. 2 schematically illustrates embodiments of the system 400 for performing tissue resection in a patient. The system 400 may comprise a treatment probe 450 as described herein and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such the treatment or imaging probe can be desirably rotated and translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 424. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

In some embodiments, the console 420 comprises impedance sensor circuitry 220 coupled to the energy source to measure impedance of tissue treated with energy from the energy source. In some embodiments, the energy source comprises an electrode and the electrode comprises an impedance sensor. In some embodiments, the processor is configured with instructions to adjust an amount of energy from the energy source in response to an amount of impedance. In some embodiments, the processor is configured with instructions to adjust an amount of deflection of the extension and offset of the energy source from the elongate axis in response to impedance.

In some embodiments, the console 420 comprises force sensor circuitry 210 coupled to a force sensor on the treatment probe. The force sensor can be coupled to the extension to measure tissue resistance related to deflection of the extension, for example. In some embodiments, the force sensor is coupled to the link to measure tissue resistance related to movement of the energy source away from the elongate axis. In some embodiments, the force sensor is coupled to the energy source to measure tissue resistance related to a positioning distance of the energy source from the elongate axis. In some embodiments, the force sensor is configured to measure tissue resistance related to an amount of energy delivery from the energy source.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450.

The probe 450 may comprise any suitable number of energy sources and configurations of energy sources. In some embodiments, the probe comprises an energy source 250 that can be offset from the elongate axis 451 the probe with an offset 252 a distance to treat tissue, for example with deflection of an extension. An example of a suitable energy source with deflection, translation and rotation to treat remove a volume of tissue is described in PCT/US2022/025617, filed on Apr. 20, 2022, entitled "SURGICAL PROBE WITH INDEPENDENT ENERGY SOURCES", published as WO/2022/226103 on Oct. 27, 2022, the full disclosure of which has been previously incorporated herein by reference. Alternatively or in combination, the probe 450 may comprise an energy source 200 such as a nozzle, and the energy source 200 may comprise any suitable energy source as described herein such as a directional energy source that emits energy along a path in a direction for the selective treatment of tissue. Examples of suitable energy sources to treat tissue with a directional energy source such as a water jet are described in "PCT/US2015/048695, filed Sep. 5, 2015, entitled "PHYSICIAN CONTROLLED TISSUE RESECTION INTEGRATED WITH TREATMENT MAPPING OF TARGET ORGAN IMAGES", published as WO2016037137, the full disclosure of which has been previously incorporated herein by reference.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed at a substantially constant distance 437 to the anchor 24. The substantially fixed distance 437 between the anchor 24 and the fixed first portion 432 of the linkage allows the treatment to be accurately placed. The first portion 432 may comprise a linear actuator to accurately position the second energy source such as high-pressure nozzle 200 in the energy delivery region 20 at a desired axial position along an elongate axis 451 of treatment probe 450. Additional actuators and linkages can be provided and operatively coupled to the processor to offset, rotate, and translate the first energy source 250 as described herein.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust with translation 418 of the probe in response to computer control to set a target location along the elongate axis 451 of the treatment probe. In some embodiments, the first portion of the linkage remains fixed, while the second portion 434 adjusts the position of the energy delivery region 20 along the axis 451. The third portion 436 of the linkage adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 425.

In order to facilitate precise control of the treatment probe and/or the imaging probe during treatment of the patient, one or more the treatment probe or the imaging probe may be coupled to a robotic, computer-controllable arm. For example, referring to system 400 shown in FIG. 2, one or both of the first arm 442 coupled to the treatment probe 450 as described herein and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

The robotic arm may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic arms, the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

Figures 3A, 3B, 3C:
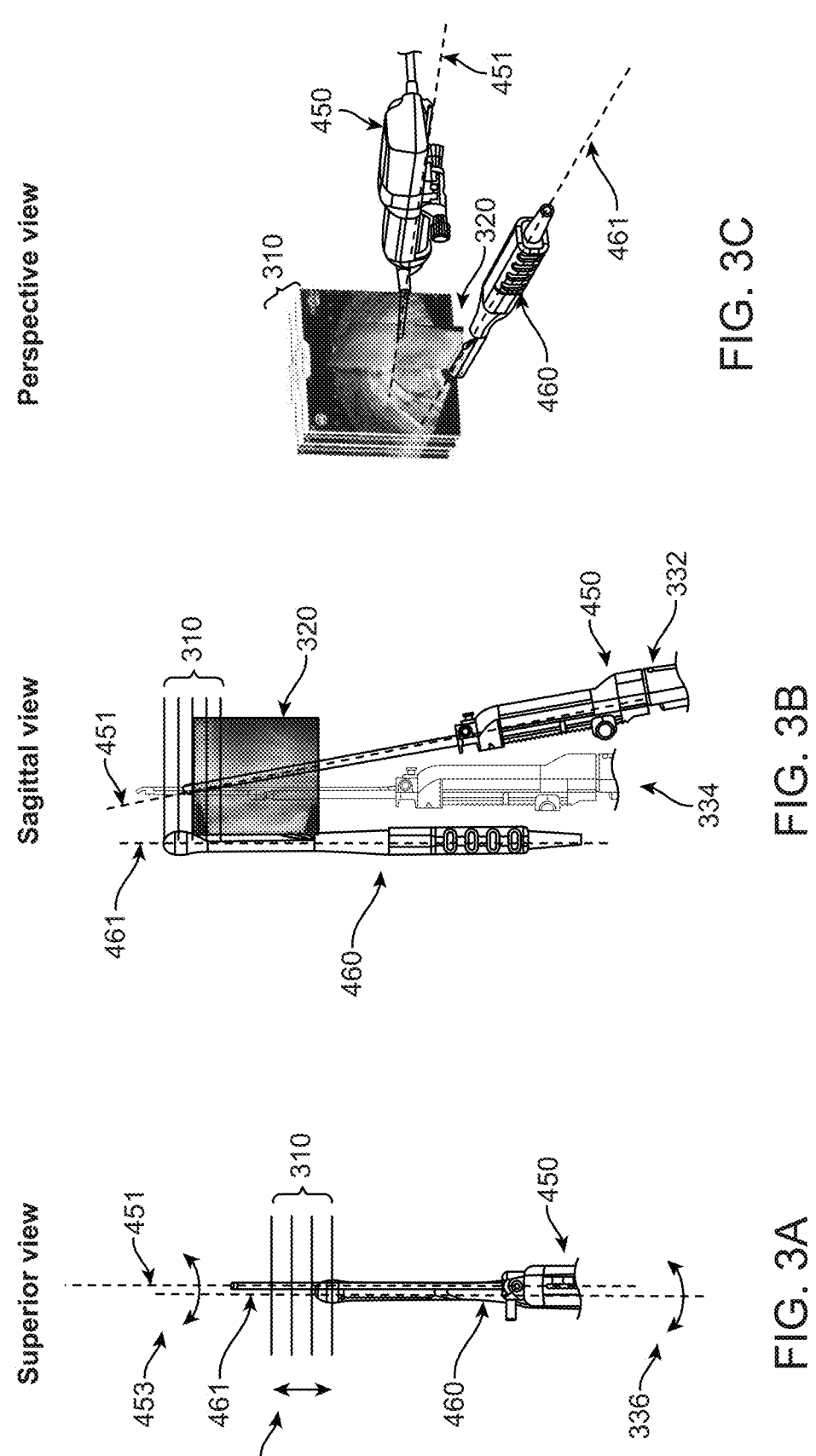
FIG. 3A shows a superior view of an arrangement of probes, in accordance with some embodiments.
FIG. 3B shows a longitudinal view such as a sagittal view of an arrangement of probes, in accordance with some embodiments.
FIG. 3C shows a perspective view of an arrangement of probes, in accordance with some embodiments.

FIGS. 3A, 3B, and 3C show superior, longitudinal (e.g. sagittal), and perspective views, respectively, of an arrangement of probes for use in treatment of tissue. In particular, FIGS. 3A, 3B, and 3C show the relative arrangement, including position and orientation of a treatment probe 450 with respect to the position and orientation of an imaging probe 460 for the treatment of tissue such as prostate tissue. The imaging probe 460 can be configured to generate transverse images such as transverse ultrasound images 310 and one or more longitudinal images such as one or more longitudinal (e.g. sagittal) ultrasound images 320. In some embodiments, the energy source of treatment probe 450 is moved with rotation angle 453 and translation 418, such that the treated tissue and the energy source are within the field of view of the imaging probe 460.

As shown in the superior view of FIG. 3A, the treatment probe axis 451 and the imaging probe axis 461 are positioned in a substantially coplanar configuration, such that the imaging probe and the treatment probe extend along a common plane. As shown in the superior view of FIG. 3B and the perspective view of FIG. 3C, the treatment probe axis 451 and the imaging probe axis 461 are positioned in a substantially coplanar and non-parallel configuration, such that the imaging probe and the treatment probe substantially extend along a common plane, which allows the imaging probe to image the treatment probe along the length of translation 418 with one or more longitudinal images such as real time longitudinal images, for example real time sagittal images. In some embodiments, the treatment probe and the imaging probe are arranged in a substantially coplanar configuration, and the ultrasound probe is rotated to rotate the longitudinal (e.g. sagittal) field of view of the imaging probe in order to image the treatment probe along a length of the longitudinal field of view. Referring again to FIG. 3A, the imaging probe 460 can be rotated about elongate axis 461 by an angle 336 to align the treatment probe 450 so as to be within the longitudinal field of view, such that the longitudinal field of view of the imaging probe is aligned with elongate axis 451 of the treatment probe, for example.

One or more of the treatment probe or the imaging probe can be moved to adjust alignment between the imaging probe and the treatment probe. In some embodiments, the proximal portion of treatment probe is moved from a first position to a second position. Referring again to FIG. 3B, the treatment probe 450 can be moved from a first position 332 to a second position 334 to adjust alignment between the probes, for example based on data from one or more fiducials as described herein.

In some embodiments, the imaging probe 460 and the treatment probe 450 are aligned to be substantially coplanar with each other within a margin of error so that the imaging probe 460 can image the treatment probe 450 and the treatment probe's energy source during treatment, for example with the treatment probe located within a field of view of the imaging probe such as a longitudinal (e.g. sagittal) image field of view. In some embodiments, the treatment probe is aligned with the imaging probe, such that the treatment probe is visible along a length of a longitudinal (e.g. sagittal) view of the imaging probe.

In some embodiments, the imaging probe 460 and the treatment probe 450 may be somewhat misaligned, e.g. by more than the margin of error, such that the treatment probe may disappear from a portion of the longitudinal (e.g. sagittal)) image because part of the imaging probe extends beyond the longitudinal (e.g. sagittal) field of view, for example. In some embodiments, this may result in the imaging probe 460 not imaging a portion of the treatment with longitudinal (e.g. sagittal) images. In some embodiments, the treatment probe 450 and the imaging probe 460 may be arranged in a substantially skewed orientation as described herein, e.g. outside the margin of error, such that the treatment probe extends outside the longitudinal (e.g. sagittal) field of view of the imaging probe but is located within the field of view of transverse images of the imaging probe. In such embodiments, the treatment can be monitored in real time with transverse images, in which the imaging probe moves to maintain the energy source and concurrently treated tissue within the transverse field of view of the imaging probe. In some embodiments, a transverse view of the tissue and energy source can decrease sensitivity to alignment between the two probes, and the imaging probe can be moved with the energy source, for example synchronously, to image the tissue and the energy source during treatment.

Figure 3D:
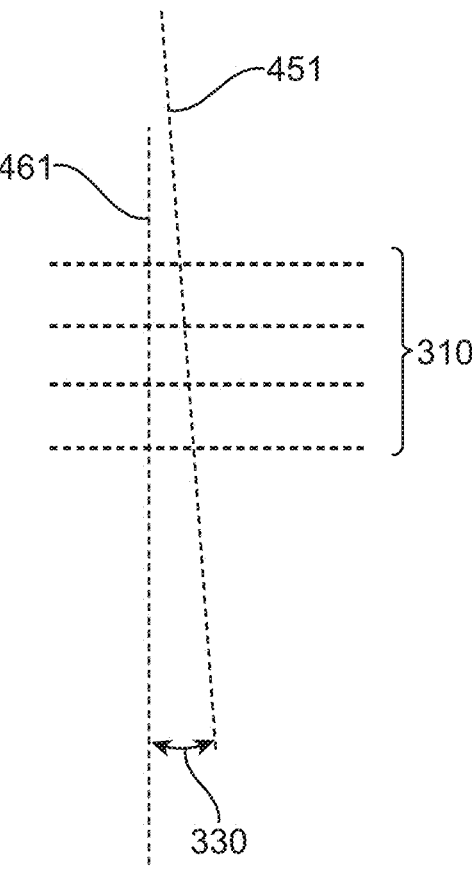
FIG. 3D shows a treatment probe axis and an imaging probe axis skewed with respect to each other by an angle, such that the treatment probe and the imaging probe do not extend along a common plane, in accordance with some embodiments.

FIG. 3D shows the treatment probe axis 451 and the imaging probe axis 461 skewed with respect to each other by an angle 330, such that the treatment probe and the imaging probe do not extend along a common plane. By adjusting the treatment probe or the imaging probe, or both, this skew angle can be decreased. The amount of acceptable skew may depend on several factors such as the field of view of the imaging probe, the length of tissue treated with the one or more of rotating or translating energy source. In some embodiments, the margin of error of the skew angle is any one of no more than 10 degrees, no more than 5 degrees, no more than 3 degrees, no more than 2 degrees, or no more than 1 degree, for example. In some embodiments, the margin of error of alignment corresponds to a longitudinal (e.g. sagittal) field of view of the imaging probe and a skew angle between the imaging probe and the treatment probe. When the treatment probe and the imaging probe are aligned within the margin of error, the treatment probe is located within the longitudinal (e.g. sagittal) field of view along the translation length of the treatment and can be viewed in one or more real-time longitudinal (e.g. sagittal) images along a length of the longitudinal (e.g. sagittal) field of view. When the treatment probe and the imaging probe are aligned outside the margin of error, a portion of the treatment probe is located outside the longitudinal (e.g. sagittal) field of view and may disappear from a portion of an image along a length of the longitudinal (e.g. sagittal) field of view. In such embodiments, transverse imaging can be used to view the treatment in real time as described herein.

Figures 4A, 4B, 4C, 5:
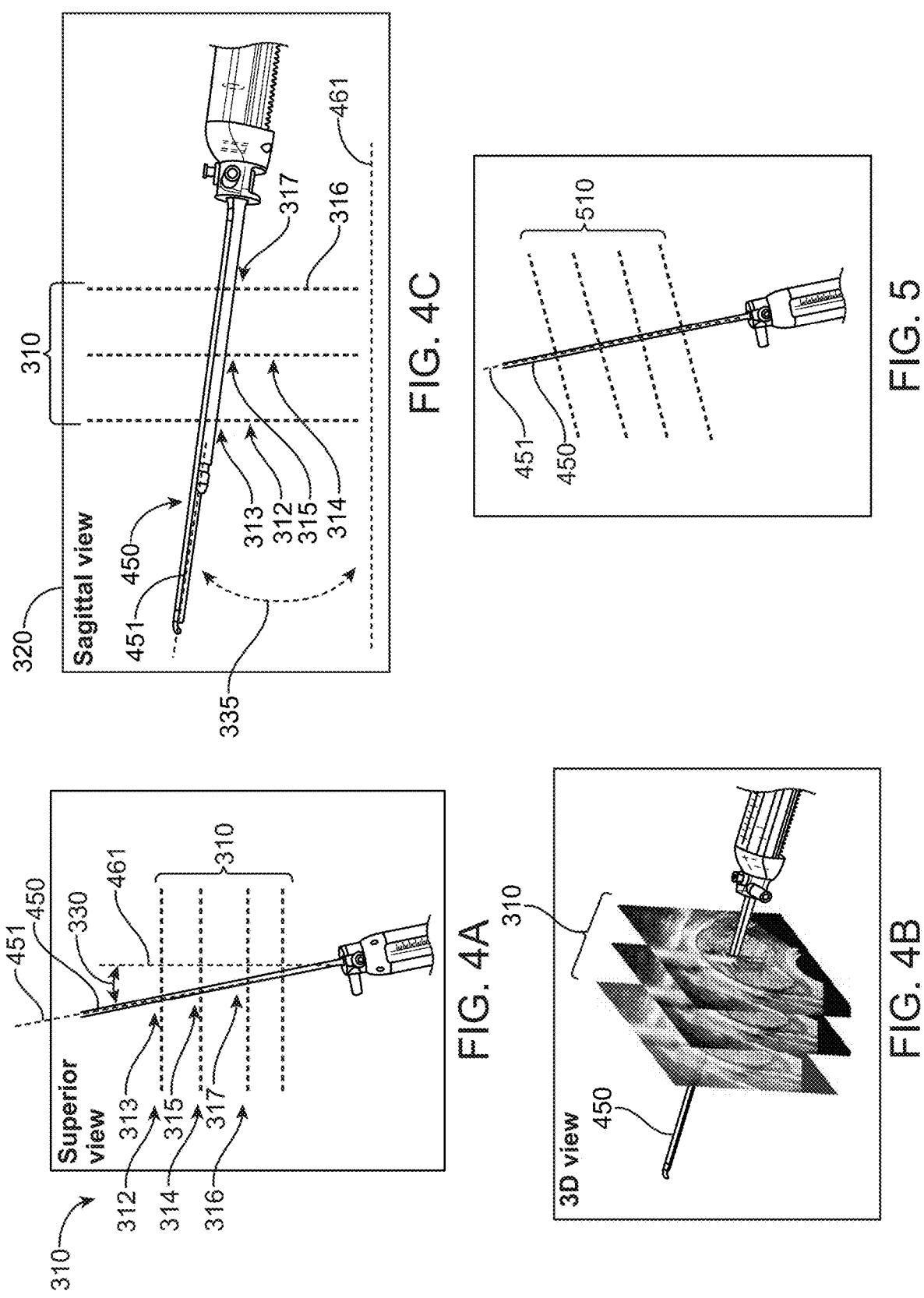
FIG. 4A shows a superior view of transverse image planes with respect to an axis of the treatment probe, in accordance with some embodiments.
FIG. 4B shows a three dimensional view of transverse image planes with respect to a treatment probe, in accordance with some embodiments.
FIG. 4C shows a longitudinal view such as a sagittal view of a treatment probe, in accordance with some embodiments.
FIG. 5 shows transverse image planes rotated with respect to an elongate axis of a probe, in accordance with some embodiments.

FIG. 4A shows a superior view of transverse image planes with respect to an axis of the treatment probe. In some embodiments, the axis 451 of imaging probe 450 comprises a non-coplanar orientation with respect to the elongate axis 461 of the imaging probe, for example with a skew angle 330. In some embodiments, the transverse images 310 comprise a plurality of transverse images such as a first transverse image 312, a second transverse image 314, and a third transverse image 316.

In some embodiments, the position of the treatment probe in the plurality of transverse images changes. The extent to which the probe position changes can be related to a non-parallel angle such as skew angle 330 between the treatment probe and the imaging probe. In some embodiments, the treatment probe 450 extends through the plane of the first transverse image 312 at the first location 313, through the plane of the second transverse image 314 at the second location 315, and through the plane of the third transverse image 316 at the third location 317. In some embodiments, the skew angle 330 results in the lateral position of the treatment probe changing in the transverse images 330, such as the pixel column location of the transverse images.

FIG. 4B shows a three dimensional view of transverse images 310 and the corresponding planes of the transverse images with respect to treatment probe 450.

FIG. 4C shows the longitudinal (e.g. sagittal) image 320 of the treatment probe 450. In some embodiments, the axis 451 of the treatment probe 450 extends at an angle 335 with respect to the elongate axis 461 of the imaging probe. In some embodiments, the angle 335 corresponds to an angle of the axis 451 of the treatment probe 450 along the longitudinal (e.g. sagittal) plane of the image. This angle may result in in the treatment probe appearing inclined in the longitudinal (e.g. sagittal) image, the position of the probe 450 changing in the transverse images 310, for example. In some embodiments, the treatment probe is sufficiently coplanar with the imaging probe so as to be located within the longitudinal (e.g. sagittal) field of view of the imaging probe along a length of the longitudinal (e.g. sagittal) field of view, even though the position of the probe changes along longitudinal (e.g. sagittal) image 320 and the corresponding transverse images 310. In some embodiments, the angle 335 results in the vertical position of the treatment probe changing in the transverse images 310, such as a pixel row location in the transverse images. In some embodiments, the treatment probe 450 shown in the longitudinal (e.g. sagittal) image extends through the plane of the first transverse image 312 at the first location 313, through the plane of the second transverse image 314 at the second location 315, and through the plane of the third transverse image 316 at the third location 317. Although reference is made to the treatment probe at a skew angle with respect to the imaging probe, in some embodiments, the angle 335 corresponds to a 3D vector projection of the treatment probe axis onto the longitudinal (e.g. sagittal) image plane of the field of view, for example. In some embodiments, the skew angle 330 corresponds to a 3D vector projection of the treatment probe axis onto a plane that is perpendicular to the longitudinal (e.g. sagittal) image plane field of view.

In some embodiments, the position of the probe in the transverse images can be used to determine one or more of the three dimensional position or the three dimensional orientation of the treatment probe with respect to the imaging probe. In some embodiments, the two dimensional location of the probe 451 is determined in each of the plurality of transverse images, and these two dimensional locations are used to determine the three dimensional orientation of treatment probe with respect to the imaging probe. The two dimensional location of the probe in each transverse image may comprise any suitable two dimensional location such as X and Y locations or pixel locations such as pixel row location and a pixel column location in each image, for example. In some embodiments, the 3D orientation of the treatment probe with respect to the imaging probe comprises a 3D vector representation of the orientation, for example.

The three dimensional orientation of the treatment probe can be used to facilitate treatment planning, for example by generating rotated transverse images. The rotation of the image data set can also be used to generate one or more rotated longitudinal images, e.g. one or more rotated sagittal images. The one or more longitudinal images can be rotated such that the position of the treatment probe remains substantially fixed along the one or more longitudinal images and the plurality of transverse images. In some embodiments, the rotated longitudinal and transverse images are generated from a 3D tomographic image data set, such as a Digital Imaging and Communications in Medicine (DICOM) image data set, by selecting the planes of the plurality of transverse images and one or more longitudinal images by generating the images along planes that are oriented at angles relative to the planes X, Y and Z planes of the 3D tomographic image dataset.

FIG. 5 shows rotated transverse images 510, which correspond to the transverse images 310 rotated to compensate for the skew angle 330 between the elongate axis of the treatment probe and the imaging probe. In some embodiments, the three dimensional orientation of the treatment probe with respect to the imaging probe can be used to rotate the transverse images such that the rotated transverse image planes are substantially perpendicular to the elongate axis 451 of the treatment probe 450, for example to within one or more of 5 degrees of perpendicular, 3 degrees of perpendicular, 2 degrees of perpendicular, 1 degree of perpendicular, 0.5 degrees of perpendicular, or 0.25 degrees of perpendicular, for example. The one or more longitudinal images such as one or more sagittal images can be similarly rotated to compensate for the angle 335. In some embodiments, the transverse images 310 and one or more longitudinal images 320 comprise images of a 3D image data set, such as Digital Imaging and Communications in Medicine (DICOM) images. The 3D vector orientation of the treatment probe with respect to the imaging probe can be used to rotate the transverse and one or more longitudinal images, such that the location of the treatment probe remains substantially fixed in the transverse images, which can facilitate treatment planning as described herein. In embodiments the rotation of the 3D image data set results in the probe appearing at a substantially fixed elevation in the one or more longitudinal images such as one or more sagittal images, for example.

Figures 6A, 6B, 6C:
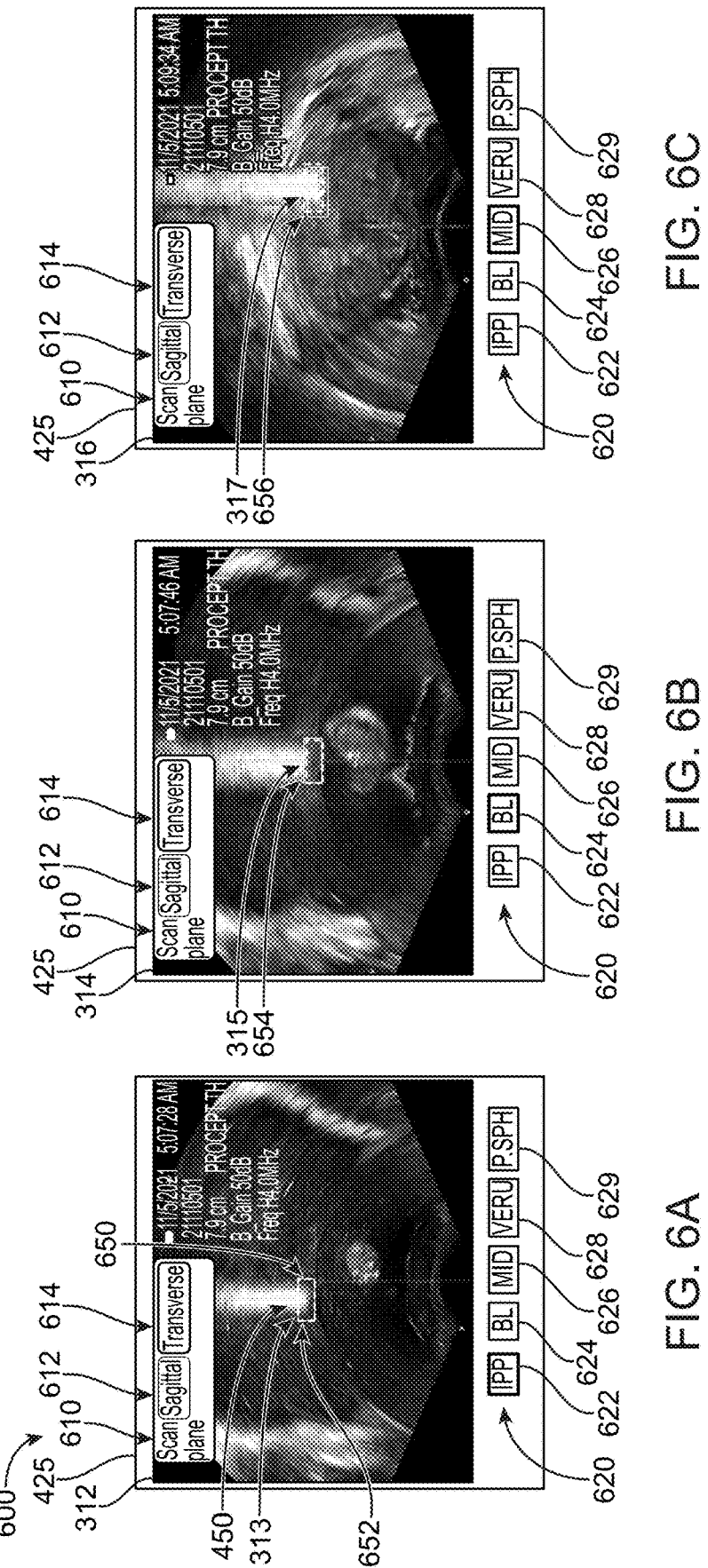
FIGS. 6A to 6C show a user interface and transverse images that show movement of a probe location in the transverse images, in accordance with some embodiments.

FIGS. 6A to 6C show a user interface 600 and transverse images that show movement of the probe location in the transverse images, which can be related to orientation of the treatment probe with respect to the imaging probe. FIG. 6A shows the transverse image 312 and the location 313 of the treatment probe 450 in the image. FIG. 6B shows the transverse image 314 and the location 315 of the treatment probe in the image. FIG. 6C shows the transverse image 316 and the location 317 of the treatment probe in the image. As will be apparent in the images, the location of the probe changes in the transverse images. The location of the probe in the transverse images can be used to determine the orientation of the treatment probe with respect to the imaging probe as described herein.

In some embodiments, a marker 650 is used to identify the location of the probe in one or more transverse images. In some embodiments, a marker is shown on each of a plurality of transverse images. In some embodiments, a first marker 652 is shown at a first location of a first transverse image, such as location 353 of the transverse image 312, a second marker 654 is shown at a second location of a second transverse image such as location 355 of transverse image 314, and third marker 656 is shown at a third location of a third transverse image such as location 317 of transverse image 316.

In some embodiments, an artificial intelligence algorithm is configured to identify the location of the probe and identify the probe with the marker that corresponds to the location of the probe. The marker may comprise any suitable marker, such as a line, mark, a series of marks, a reticle, a cross, or a geometric shape such as a triangle or polygon, e.g. a box. In some embodiments, the user interface is configured to allow the user to adjust the position of the marker, for example after reviewing an initial position determined with the algorithm as described herein.

In some embodiments, a user interface 600 is configured to show the images on the display 425 in response to user inputs. In some embodiments, user interface 600 is configured to display a scan plane 610 with an associated user input 612 for the user to select one or more longitudinal (e.g. sagittal) plane images and an associated user input 614 for the user to select the transverse images. In some embodiments, the user interface 600 comprises a plurality of user selectable inputs 620 for the user to select a transverse image for viewing on the display. The plurality of user selectable inputs 620 may comprise a separate input for each plane, such as a user selectable button, tab, or pull down menu, for example. In some embodiments, a first user selectable input 622 corresponds to a first transverse image 312 along a first plane, a second user selectable input 624 corresponds to a second transverse image 314 along a second plane, a third user selectable input 626 corresponds to a third transverse image 316 along a third plane, a fourth user selectable input 628 corresponds to a fourth transverse image along a fourth plane, and a fifth user selectable input 629 corresponds to a fifth transverse image along a fifth plane.

In some embodiments, the first user input 622 corresponds to an intravesical prostatic protrusion (IPP), the second user input 624 corresponds to the bladder neck (BL), the third user input 626 corresponds to the mid prostate (MID), the fourth user input 628 corresponds to the verumontanum (VERU), and the fifth user input 629 corresponds to the peripheral sphincter (P. SPH). Although reference is made to anatomical landmarks of the prostate, the user selectable inputs may correspond to any anatomical structure.

Although reference is made to five user inputs and five corresponding transverse images along corresponding planes, the number of inputs and corresponding images may comprise any suitable number, such as two user selectable inputs corresponding to a first transverse image and a second transverse image. Alternatively, more than five user selectable inputs and transverse images can be used.

FIG. 7A shows a user interface 700 with a three dimensional view 710 for three dimensional treatment planning. In some embodiments, an animation of the treatment probe 450 is overlaid on a plurality of 2D images such as 2D ultrasound images, which are arranged in a 3D digital environment, which allows view the images with a 3D perspective. In some embodiments, the user interface is configured for the user to select an image among the plurality of images to maximize the selected image with another view. The plurality of 2D images may comprise a plurality of transverse images 310, which are arranged along one or more longitudinal images such as one or more sagittal images 320. In some embodiments, each of the plurality of transverse images 310 is located along the one or more longitudinal images such as one or more sagittal images 320 at a position corresponding to an intersection of the transverse image and the one or more longitudinal (e.g. sagittal) images, such as an intersection in a 3D data set. In some embodiments, the user interface 700 is configured for a user to select an image to maximize a view of the image, for example by clicking on the image, and provide an enlarged view of the image. For example, the user can select one or more of the longitudinal (e.g. sagittal) images or a transverse image to view the selected image with an enlarged view.

In some embodiments, an AI algorithm is used to identify tissue structures and develop a 3D treatment plan, such as a 3D treatment profile as described herein.

The treatment profile 730 may comprise an animated treatment profile, which allows the user to view the treatment profile from different perspectives, angles and images, for example. In some embodiments, the user is provided with a control to one or more of zoom, pan, or rotate the perspective view. In some embodiments, the treatment profile 730 comprises an animated treatment profile that matches the one or more of the zoom, pan or rotation of the perspective view, such that alignment of the treatment profile with the plurality of images is maintained. This approach can allow the user to view the treatment profile and its relationship with corresponding tissue from any suitable perspective. In some embodiments, the animated treatment profile is configured to generate simulation of the treatment with movement of the energy source and an increasing volume of treatment tissue, such similar to movie that simulates the treatment.

In some embodiments, the user interface 700 is configured for the user to adjust the treatment profile, and the treatment profile is automatically updated and shown on the perspective view and other selected images, for example simultaneously updated in real time. The user interface may comprise an input 755 such as a visible icon that the user can drag to change the position of the treatment profile. In some embodiments, the user interface 700 is configured with an input 755 such as a 3D input for the user to adjust the treatment profile shown in the 3D view. In some embodiments, when the treatment profile is adjusted in one of the views with the user input, the treatment profile is automatically updated in the other views, for example simultaneously updated, so that the user can evaluate the change in the treatment profile from more than one perspective. In some embodiments, the treatment profile comprises a plurality of curved lines, such as splines, that are updated together and shown on the different views.

FIG. 7B shows a longitudinal view (e.g. sagittal) view 720 for three dimensional treatment planning. In some embodiments, a longitudinal treatment profile such as a sagittal treatment profile 732 is overlaid on one of the one or more longitudinal images such as on one of the one or more sagittal images 320. While the user interface 700 can be configured in many ways, in some embodiments the user is presented with longitudinal view 720 and a 3D perspective view 710, for example. In some embodiments, the user interface is configured for the user to select the image from the one or more images longitudinal (e.g. sagittal) images 320 from the perspective view and provide the longitudinal (e.g. sagittal) view of the image as shown in FIG. 7B.

In some embodiments, the 3D treatment profile 730 is updated in response to the user input such as a 3D user input, and the corresponding sagittal treatment profile 732 and transverse treatment profile 734 of the 3D treatment profile updated in the corresponding views such as the longitudinal and transverse views as described herein. For example, the longitudinal (e.g. sagittal) treatment profile 732 can be updated with user input 755 on the 3D view 710 to move the longitudinal treatment profile 732 from a first longitudinal treatment profile to a second longitudinal treatment profile 782, and the updated treatment profile will be shown in the other views, such as the longitudinal (e.g. sagittal) view as shown in FIG. 7B. Similarly, the 3D treatment profile 730 can be adjusted in the longitudinal (e.g. sagittal) view 720 from a first longitudinal treatment profile 732 to a second longitudinal (e.g. sagittal) treatment profile 782 and the updated treatment profile shown in the 3D view 710. The treatment profiles in the transverse views can be similarly adjusted updated and shown in the 3D view and longitudinal (e.g. sagittal) views, for example.

The one or more longitudinal images 320 shown in the 3D view can be configured in many ways and may comprise any suitable number of longitudinal images, such as a single longitudinal image or a plurality of longitudinal images, for example. The one or more longitudinal images may comprise one or more sagittal or parasagittal images, for example. In some embodiments, the user interface 700 is configured to receive a user input identifying a selected image among the one or more longitudinal images 320 and the plurality of transverse images shown in the 3D view and display the selected image with a 2D view.

In some embodiments, the one or more longitudinal images comprises a plurality of longitudinal images. In some embodiments, the user interface 700 is configured for the user to select one or more longitudinal images 320 from a plurality of longitudinal images. In some embodiments, the user interface 700 is configured for a user to select a longitudinal image in the 3D view. For example, the user interface 700 can be configured for the user to select the longitudinal image with a pointing device our touching the image on a touch screen display as described herein. Alternatively or in combination, the plurality of inputs 620 may comprise a plurality of inputs corresponding to a plurality of longitudinal images. Alternatively or in combination the user input 724 may comprise a plurality of inputs configured for a user to select a plurality of longitudinal images for display in a plurality of 2D views.

While the plurality of longitudinal images can be generated in many ways, in some embodiments the plurality of longitudinal images has been generated from a 3D volumetric image of the tissue as described herein.

In some embodiments the plurality of longitudinal images has been generated in response to a plurality of angles of an energy source to treat the tissue. In some embodiments, the 3D treatment profile 730 corresponds to a plurality of rotations and translations of the energy source on the probe 450 as described herein, and at least one of the plurality of longitudinal angles corresponds to a rotation angle of the energy source.

FIGS. 7C and 7D show a plurality of rotational angles relative to the treatment probe that can be used to generate a plurality of longitudinal images. The plurality of longitudinal images may comprise longitudinal images corresponding to rotation angles the energy source of the treatment probe 450 about axis 451. For example, 3D view may comprise a first longitudinal image 320a of the one or more images 320 corresponding to a first rotational angle 770 of the energy source, and a second longitudinal image 320b corresponding to a second rotational angle 772 of the energy source as shown in FIG. 7B.

In some embodiments, plurality of longitudinal images comprises a first longitudinal image 320a along a first portion 732a of the treatment profile and a second longitudinal image 320b along a second portion 732b of the treatment profile.

In some embodiments, the arrangement in the 3D view shows a portion of the first longitudinal image along the first portion of the treatment profile and a portion of the second longitudinal image along the second portion of the treatment profile. In some embodiments, the image 320b is placed in the 3D view 710 at the angle 772, and the image 320a is also shown in the 3D view 710 at the angle 770. The user can select which longitudinal images to show in the 3D view with the user interface as described herein. The plurality of longitudinal images may comprise any suitable number of images and may comprise at least 3 longitudinal images, each at a different angle of rotation with respect to an elongate axis of a treatment probe.

In some embodiments, the first longitudinal image comprises a first transparency along the first portion of the treatment profile and a second transparency along the second portion of the treatment profile greater than the first transparency to increase visibility of the second longitudinal image along the second portion. In some embodiments, the second longitudinal image comprises a first transparency along the first portion of the treatment profile and a second transparency the second portion of the treatment profile, the first transparency greater than the second transparency to increase visibility of the first longitudinal image along the first portion of the treatment profile.

In some embodiments, an AI algorithm is used to process the image data and identify one or more anatomical tissue structures and provide mark on the one or more anatomical tissue structures in one or more of the views shown on the user interface, such as on a longitudinal (e.g. sagittal) view and a transverse view. In some embodiments, a mark such as mark 750 is shown on the one or more of the transverse images 310 of the 3D perspective view, and the mark 750 can be shown on the corresponding transverse view. In some embodiments, a mark such as mark 760 corresponding to one or more anatomical tissue structures is shown on the one or more longitudinal views 720 of one or more longitudinal images such as one or more sagittal images 320, for example. The mark 750 and the mark 760 may generally comprise any suitable change to the pixels overlaid on the image, such as one or more of highlighting, dashes, lines, icons or other features so as to indicate the profile identified with the AI algorithm.

In some embodiments, a plurality of views is shown simultaneously on the user interface, for example the 3D perspective view of FIG. 7A and the one or more longitudinal views of FIG. 7B. Alternatively or in combination, the 3D perspective view can be shown with one or more transverse views. The plurality of views can be arranged in any suitable way, for example a side by side configuration, or a view inside a view configuration, for example. In some embodiments, each of the user selectable views is shown in a pop up window that the user can one or more of move, resize, or close, for example.

In some embodiments, the user interface 700 comprises an input 712 for the user to select the three dimensional view and an input 724 for a user to select one or more longitudinal views such as one or more sagittal views 720, and a treatment profile such as a 3D treatment profile 730 is overlaid on the images. In some embodiments, the 3D treatment profile comprises a plurality of transverse treatment profiles 734 and one or more longitudinal (e.g. sagittal) profiles 732, which can be overlaid on the corresponding images. The user interface 700 may comprise one or more features of user interface 600, for example.

In some embodiments, the images shown in user interface 700 comprise rotated images such as images from a rotated 3D image, in which the images have been rotated in response to an orientation between the imaging and treatment probe as described herein. Alternatively, the images may comprise unrotated images, such as unrotated 3D images, for example.

FIG. 8A shows a first transverse view 742 for three dimensional treatment planning at a first depth of the three dimensional treatment profile 730. The first transverse view 742 may comprise a view from among a plurality of user selectable transverse views. In some embodiments, the first transverse view 742 corresponds to a transverse image of the IPP of the prostate, although the first view may comprise any transverse view at any suitable depth of any suitable tissue. The user interface 700 may comprise a plurality of inputs for the user to adjust the 3D treatment profile from the transverse view. The inputs may comprise a first two dimensional input 812 to adjust a first side of the transverse treatment profile 734, and a second user input 814 to adjust the second side of the transverse treatment profile. The user interface can be configured to provide information related to the treatment profile, such as a depth 820 of the treatment profile 734 from the probe, and an angle 822 of the treatment profile, which may correspond an angular sweep angle of a scan of the energy source along the tissue. In some embodiments, the treatment profile comprises an angular subtense, such as a subtending line of the angle of the treatment profile with respect to the axis 451, which may correspond to a location of the energy source during treatment. Although reference is made to angular treatment profile with a corresponding radius, the treatment profile may comprise other shapes as described herein.

In some embodiments, the other views are updated in response to adjustments to the treatment profile as described herein. For example, input 814 can be used to adjust the treatment profile 734 from a first position to a second position 816 or a third position 818, and the other views such as the 3D view automatically updated, for example updated substantially simultaneously and in real time, e.g. within a few seconds for example.

FIG. 8B shows a second transverse view 744 for three dimensional treatment planning at a second depth of a three dimensional treatment profile. In some embodiments, the first transverse view 742 and the second transverse view 744 comprise images from among a plurality of user selectable views such as user selectable transverse views as described herein. In some embodiments, the second view corresponds to a transverse image of MID prostate, although the second view may comprise any transverse view at any suitable depth. In some embodiments, the second view comprises a different view than the first view at a different depth than the first depth. The second transverse view 744 may comprise a similar user interface to that shown in FIG. 8A for adjusting the treatment profile 734, and the other views automatically updated as described herein.

FIG. 9A shows transverse view a probe 450 and a plurality of rotational angles 932 of an energy source 200 on the probe to direct the energy source 200 toward the tissue 910 to treat the tissue to different depths in accordance with a treatment plan. In some embodiments, a 3D treatment plan is determined from a plurality of transverse images, in which the angles and treatment depths from each of the plurality of transverse images are combined to generate the 3D treatment plan. The plurality of rotational angles 932 can be referenced with respect to a reference 930, which may comprise fixed a reference such as a horizontal or vertical reference for example. While the treatment plan can be determined in many ways, in some embodiments the plurality of rotational angles 932 can be evaluated with a plurality of projections 940 from the probe at the plurality of angles 932. In some embodiments, the projections correspond to angles of the directional energy source 200 that can be rotated with respect to the probe axis 451. The plurality of projections 420 may comprise any suitable number of projections such as first projection 942, a second projection 944, a third projection 946, a fourth projection 947, a fifth projection 968 and a sixth projection 969, for example for example. Although reference is made to projections to describe aspects of the treatment plan and planning, the treatment angles and depths as described herein can be determined in many ways as will be understood by one of ordinary skill in the art.

In some embodiments, the angular width and thickness of the tissue is determined at a plurality of angles 932 of the treatment probe 450, for example at a plurality of angles of the directional energy source, such as a plurality of angles of a nozzle, light beam or other energy source as described herein. In some embodiments, a thickness of tissue to be treated is determined with respect to angular coordinates of the treatment probe. In some embodiments, the width of the tissue in the transverse view comprises an angular width, such as an angular width between a first angle 934 and a second angle 936. In some embodiments, the first angle 932 corresponds to a projection such as a projection 944 and the second angle 926 corresponds to a projection such as projection 948. In some embodiments, the treatment plan is configured to treat the tissue between the first treatment angle 934 and the second treatment angle 936, for example without treating tissue outside of these angles at the translational position corresponding to the image, which can decrease interaction with the second tissue 420.

In some embodiments, the thickness profile comprises a thickness at each of a plurality of angles, and the thickness profile may be used to develop the treatment plan. In some embodiments, the treatment plan is configured to selectively direct energy from the energy source to the tissue in accordance with a depth of the tissue at a corresponding angle. In some embodiments, the treatment plan is configured not to direct energy toward the tissue at angles corresponding to a thickness of zero, which can decrease interaction of the energy source with a second tissue, such as second tissue 920, for example.

In some embodiments, the thickness comprises a distance through the tissue at a corresponding angle. For example, the thickness may comprise a distance between a first location 962 and a second location 964 at a corresponding angle such as an angle corresponding to second projection 944. In some embodiments, a first distance from the treatment probe 450 to the first location 962 and a second distance from the treatment probe 450 to the second location 964 are used to determine the treatment plan. In some embodiments, the first location 962 and the second location 964 comprise a first location of the boundary 912 with an outer surface facing toward the probe at the corresponding angle, and a second location of the boundary 912 with an outer surface facing away from the probe at the corresponding angle. In some embodiments, the tissue 910 is located at a distance from the probe, for example with the first location 962 of the boundary 912 located a distance from the probe. In some embodiments a gap extends between the treatment probe and the boundary, and the gap may comprise a bodily fluid as described herein, such as urine for example.

In some embodiments, data related to the projections 940 of the energy source at the plurality of angles can be used to generate the treatment plan and may be adjusted to more accurately treat the tissue, for example to remove the tissue, e.g. with tissue resection or ablation. In some embodiments, a first margin 952 of the tissue boundary 910 is determined with respect to the treatment probe 450, and a second margin 954 of tissue 910 is determined with respect to the treatment probe. In some embodiments, the first margin 952 of the tissue boundary 912 is determined with respect to the treatment probe 450, and the second margin 954 of boundary 912 is determined with respect to the treatment probe. In some embodiments, the first margin 952 and the second margin 954 are located on opposite sides of the area 914 tissue 910. For example, the first margin 952 can be located on the first side 916 of the area 914, and the second margin 954 can be located on a second side 918 of the area 914.

In some embodiments, the angles of the treatment plan are determined in response to the angles of the boundary. In some embodiments, the angles of the treatment plan are configured to provide a margin of tissue near the boundary. In some embodiments, the treatment plan is configured to adjust the treatment angles to limit the treatment so as not to extend beyond the first boundary margin 952 and the second boundary margin 954. In some embodiments, the user interface is configured to provide a notification to the user if the treatment plan extends beyond the angular boundary, for example if the treated tissue is in proximity to an untreated tissue. In some embodiments, the tissue margins are located outside an outer portion of the area to be treated. Alternatively or in combination, the treatment plan can be configured to treat tissue at the tissue boundary, for example if it is beneficial to fully remove the treated tissue. In some embodiments, the treatment plan is configured to treat the tissue up to the tissue boundary along a first portion of the treatment and to provide a tissue margin along a second portion of the treatment.

While the first boundary margin 952 and the second boundary margin 954 can be determined in many ways, in some embodiments the location of the first boundary margin 952 corresponds to a first projection, such as projection 942, that intersects the boundary 912 tangentially at a point to define the boundary margin 952, and the second boundary margin 954 corresponds a second projection, such as projection 948, that intersects the boundary 912 tangentially at a point to define the boundary margin 954, for example. In some embodiments, the first boundary margin is defined by a first angle at which the projection of the first angle intersects the boundary tangentially on a first side, and the second boundary margin is defined by a second angle at which is the projection of the second angle intersects the boundary 912 tangentially on the second side, for example.

In some embodiments, the probe 450 is visible on a corresponding image such as a transverse image 312, and the image can be shown on a display 425 of user interface 700, for example. The view shown on the display may comprise any user selectable view as described herein, such as IPP view 742, for example.

In some embodiments, an image of the tissue 910 to be treated comprises a boundary 912. The boundary 912 can be identified with an AI algorithm as described herein, or by a user, and combinations thereof. In some embodiments, the tissue 910 is located near a second tissue 920, which may comprise a different anatomical structure from tissue 910 and may comprise a tissue of a different organ as described herein, for example. The second tissue 920 may comprise an identifiable boundary 922 along a surface which may be oriented toward the first tissue, for example. The boundary 912 may be identified in many ways as described herein, for example with an AI algorithm, by a user of the system, and combinations thereof. In some embodiments, the boundary 912 defines the area 914 of the tissue to be treated, and the area 914 may comprise the first side 916 and a second side 918 generally disposed on opposite sides of the area 914 to be treated. In some embodiments, the boundary 912 encloses the area 914 to be treated. Each of the aforementioned boundaries may be identified with an AI algorithm and the identified boundary shown on the display by overlaying the boundary on the images, for example by modifying pixels along the boundary such as with pixels of a different color.

In some embodiments, the treatment plan is configured to treat the tissue 910 in accordance with an angular tissue depth profile, which comprises a plurality of tissue depths at a plurality of angles. The treatment plan can be configured to adjust one or more of an intensity of energy from the energy source, a power of energy from the energy source, a translation of the probe along the treatment probe axis, a rotation of the probe about the treatment probe axis, a translational velocity of the treatment probe, a rotational velocity of the treatment probe, or a number of passes of the energy source along the tissue, in order to treat the tissue to different depths in accordance with the angular tissue depth profile. In some embodiments, an intensity of the energy source is decreased for decreased depth and increased for areas of increased depth. Alternatively, the movement of the energy source can be adjusted in response to the tissue profile and the energy from the energy source 200 remains substantially fixed, for example with a fixed flow rate from a pump such as a pulsatile pump coupled to a nozzle. In some embodiments, a power of the energy source is adjusted in response to the tissue profile, such as a flow rate from a pump or a power from a laser, for example. In some embodiments, one or more of a translational velocity or a rotational velocity of the energy source is adjusted in response to the angular tissue profile.

In some embodiments, the treatment plan is configured to scan the energy source over a region of tissue more than one time, such that the energy can be delivered to the tissue with a plurality of passes of the energy source. In some embodiments, the treatment plan is configured to successively remove a plurality of layers of tissue. In some embodiments, the treatment plan is configured to remove a first layer of tissue, for example with one or more of removal, ablation, resection, and a second layer of tissue is treated with the energy source to remove the second layer. In some embodiments, the treatment plan is configured to treat tissue to a first depth along a first removal profile 970, which extends from a first location 972 of the boundary 912 to a second location 964 of the boundary 912, for example. The treatment plan is configured to remove the second layer of tissue with another scan of the energy source to remove tissue between the first removal profile and the boundary 912. As many layers of tissue can be removed as appropriate, and the depth of removal can be determined based on several factors, such as one or more of the type of energy from the energy source, the tissue type, the distance from the energy source to the layer of tissue to be removed, the rotational velocity of the energy source, or the translational velocity of the energy source, for example. In some embodiments, the treatment plan is configured to substantially fix a translational position of the treatment probe 450 along axis 451 while the energy source is scanned across the tissue with angular rotation of the energy source at the plurality of angles 932. For example, a first layer of tissue can be removed to the depth of the first removal profile 970 and a second layer of tissue removed beneath the removal profile 970 while the translational position of the energy source remains substantially fixed. Alternatively, the energy source may be scanned with translation along the elongate axis 451 while an angle of the energy source 200 remains substantially fixed, in order to remove a plurality of layers.

In some embodiments, a treatment plan is developed for each of the plurality of images, and the treatment plans combined to generate a 3D treatment plan. In some embodiments, parameters from the treatment plan are interpolated for locations between the 3D images, for example. Alternatively or in combination, the 3D angular depth profiles from each of the plurality of images can be combined and interpolated to define a 3D angular depth treatment profile. In some embodiments, the images comprise 3D images in which the spacing between transverse view is sufficiently small that the interpolation is not performed, for example.

In some embodiments each of a plurality of images is evaluated as described herein, in order to determine a plurality of tissue removal profiles at a plurality of transverse image locations, and the removal profiles combined to generate a 3D treatment plan. In some embodiments, a plurality of tissue profiles is combined from the plurality of images and interpolated between the locations of the images.

FIG. 9B shows a probe and rotational angles and a treatment profile 980 overlaid on an image of tissue, such as one or more longitudinal or transverse images as described herein. Although a treatment plan can be generated in many ways, in some embodiments, a treatment profile 980 can be helpful to determine profiles of the treatment plan, and also to allow a user to review and modify a planned treatment. In some embodiments, the treatment profile 980 is configured to substantially match the boundary 912, e.g. to within a 5% of the diameter of the boundary. In some embodiments, the treatment profile 980 is configured to provide one or more tissue margins as described herein. In some embodiments, an AI algorithm is configured to identify the boundary 912 and overlay the treatment profile on the boundary or use the boundary 912 as the treatment profile for generating the treatment plan, for example as described with reference to FIG. 9A.

FIGS. 9C and 9D show treatment plans with one or more tissue margins 985. The one or more tissue margins may comprise one or more of an angular tissue margin 987 or a depth tissue margin 989, for example. In some embodiments, the one or more tissue margins is referenced with respect to the boundary 912, so as to decrease interaction with neighboring untreated tissue such as second tissue 920 while the first tissue 910 is treated. In some embodiments, the angular tissue margin 987 corresponds to an angle between boundary 912 and the first treatment angle 934 at the boundary of the removal profile 970. In some embodiments, the depth tissue margin 989 corresponds to a depth of tissue beyond a depth of penetration of the energy source at the first treatment angle 934. In some embodiments, the first treatment angle corresponds to a projection of the energy source, such as projection 944.

In some embodiments, the removal profile 970 is configured to provide one or more tissue margins 990 on the second side 918. In some embodiments, the second angular tissue margin 992 corresponds to an angle between boundary 912 and the second treatment angle 936 at the boundary of the removal profile 970. In some embodiments, the depth tissue margin 994 corresponds to a depth of tissue beyond a depth of penetration of the energy source at the second treatment angle 936, such as a depth of tissue at the second treatment angle beyond the depth of the removal profile 980.

In some embodiments, the treatment profile 980 corresponding to the removal profile 970 is overlaid on the image of the tissue as described herein.

In some embodiments, the user interface is configured for a user to view the treatment profile 980 overlaid on the image of the tissue 910 and allow the user to adjust the treatment profile. Alternatively or in combination, the boundary 912 identified with the AI algorithm can be marked on the display, e.g. with modified pixels, for the user to verify the locations of the boundary determined with the AI algorithm. In some embodiments, the user interface is configured to display the location of the boundary 912 determined with the AI algorithm and to display the treatment profile 980, both of which are overlaid on the image of the tissue, such as transverse image 312. The user interface can be configured for the user to select different views and images for the user to view and verify the treatment plan.

In some embodiments, the user interface is configured for the user to adjust the treatment profile in a plurality of views of the tissue as described herein. In some embodiments, it may be helpful for the user to adjust the treatment profile based on one or more of physician preferences, prior patient outcomes or patient preferences, for example. Referring again to FIG. 9B, the treatment profile 980 is shown somewhat inside the boundary 912 near the first margin 952 and the second margin 954. Such user adjustments can be helpful if the user would like to decrease interaction of the energy source with the second tissue 980, for example. Alternatively or in combination, the user can adjust other regions of the treatment profile as appropriate. A portion of the treatment profile 980 oriented toward the nozzle is shown substantially overlapping the tissue boundary 910, and another portion of the treatment profile 980 oriented toward the second tissue 420 is shown substantially overlapping the boundary 912, which can help to ensure complete treatment of the tissue at these locations, e.g. complete removal with one or more of ablation or resection for example. These regions of the treatment profile may be similarly adjusted by the user, for example so as to extend outside the boundary 912 or be located more fully within the boundary 912.

While the treatment profile 980 can be adjusted by the user in many ways, in some embodiments the user interface is configured for the user to select a location of the treatment profile and drag the location of the treatment profile to a desired position on the image. In some embodiments, the user interface is configured to drag a portion of the treatment profile to a desired location and perform a curve fit to the desired location, such that the treatment profile remains smooth and continuous, for example. Alternatively or in combination, the user interface can be configured for the user to move the entire treatment profile with respect to the tissue. The user interface can be configured to perform this selection and movement in many ways, such as with a pointing device, e.g. a trackpad or mouse, or a display such as a touch screen display for example.

Once the treatment profile has been determined, the treatment plan can be configured based on the treatment profile, similarly to the determination of the treatment plan described herein with reference to the boundary 912, such as the angle depth profile of the treatment profile with respect to the energy source 200.

FIG. 10 shows a method 1000 of planning a three-dimensional treatment (3D) with a user interface.

At a step 1010, one or more images are received. The one or more images may comprise any image or combination of images as described herein, such as a 3D image, a plurality of transverse images, or one or more longitudinal (e.g. sagittal) images, and combinations thereof.

At a step 1020, a 3D view of the one or more images is generated. The 3D view may comprise an arrangement of images, such as a plurality of transverse images arranged along one or more longitudinal images e.g. along one or more sagittal images, for example. In some embodiments, the 3D view comprises the plurality of transverse images arranged along the one or more longitudinal images at a plurality corresponding locations along the one or more longitudinal images. In some embodiments, the plurality of transverse images intersects the one or more longitudinal images at the plurality of corresponding locations. In some embodiments, the plurality of transverse images comprises volumetric pixels (voxels) overlapping with the one or more longitudinal images at the plurality of corresponding locations, for example when the received image comprises a 3D volumetric image such as a 3D ultrasound image. In some embodiments, the plurality of transverse images and the one or more longitudinal images comprise images from a 3D tomographic image. In some embodiments, each of the plurality of transverse images appears substantially perpendicular to the one or more longitudinal images in the 3D view, for example to within five degrees of perpendicular. In some embodiments, the plurality of transverse images and the one or more longitudinal images comprise ultrasound images, such as the ultrasound images comprise images from an ultrasound probe inserted into the patient.

In some embodiments, the 3D view comprises a perspective view, in which the plurality of transverse images and the one or more longitudinal images are arranged and shaped to provide a perspective to the 3D view as viewed from a distance to the user.

In some embodiments, the plurality of transverse images comprises a first portion on a first side of the one or more longitudinal images and a second portion on a second side of the one or more longitudinal images, in which the first portion is shown in front of the one or more longitudinal images and the second portion is shown behind the one or more longitudinal images. In some embodiments, wherein the one or more longitudinal images comprises an amount of transparency sufficient to view the second portion of one or more of the transverse images through the one or more longitudinal images.

At a step 1025, a representation of a treatment probe is generated. The representation may comprise an image of the treatment probe from the images received from an imaging device, a computer generated representation or an animation of the treatment probe, and combinations thereof, for example. In some embodiments, the representation of the treatment probe is shown in the 3D view extending in a sagittal direction. In some embodiments, the representation comprises a computer generated representation corresponding to a plurality of locations of translational positions and angles of rotation of an energy source, for example. In some embodiments, the representation comprises an animation of the treatment probe, for example. In some embodiments, the animation of the treatment probe is configured to move to show an animation of the treatment probe delivering energy from an energy source to tissue in accordance with a 3D treatment plan, for example in accordance with the 3D treatment profile.

At a step 1030, the 3D view is provided on the user interface. In some embodiments, the 3D view is provided to the user interface with a representation of a treatment profile overlaid on the one or more longitudinal images and one or more of the plurality of transverse images. While the representation can be shown in many ways, in some embodiments, the representation is shown at locations where the representation of the 3D treatment profile intersects the images.

At a step 1035, the 3D view is adjusted. While the 3D view can be adjusted in any way as described herein, in some embodiments the 3D view is adjusted with user manipulations of a user input device such as a pointing device or touch screen display. In some embodiments, the relative positions and orientations of the images shown in the 3D view changes in response to the user input. In some embodiments, the plurality of transverse images comprises a first portion on a first side of the one or more longitudinal images and a second portion on a second side of the one or more longitudinal images, in which the first portion is in front of the one or more longitudinal images and the second portion is behind the one or more longitudinal images.

In some embodiments, the arrangement comprises a three dimensional (3D) arrangement and the user interface comprises an input for a user to one or more of zoom, pan or rotate the 3D arrangement in the 3D view. In some embodiments, the user input is configured to rotate the one or more longitudinal images and the plurality of transverse images from a first orientation to a second orientation. The first orientation shows a first portion of the plurality of transverse images in front of the one or more longitudinal images and a second portion of the plurality of transverse images is behind the one or more longitudinal images, and the second orientation shows the second portion of the plurality of transverse images in front of the one or more longitudinal images and the second portion of the transverse images behind the one or more longitudinal images.

At a step 1040, a user input is received to select the view(s) to display. The selected view may comprise any suitable view as described herein such as a plurality of transverse views, a sagittal view, or a 3D view, and combinations thereof. In some embodiments, the user selectable views comprise one or more of a plurality of transverse images, for example. In some embodiments, the user interface is configured to receive a user input selecting a transverse image among the plurality of transverse images and provide a two dimensional (2D) view of the transverse image with the representation overlaid on the 2D view of the transverse image in response to the user input. In some embodiments, the user interface is configured to receive a user input selecting the one or more longitudinal images and provide a 2D view of the one or more longitudinal images with the representation overlaid on the 2D view of the one or more longitudinal images in response to the user input, for example.

In some embodiments, wherein the user interface is configured to receive a user input identifying a selected image among the one or more longitudinal images and the plurality of transverse images shown in the 3D view and display the selected image with a 2D view. In some embodiments, the user input corresponds to a location of the selected image in the 3D view and a user input at the location with a pointing device or a touch screen display. Alternatively or in combination, the user interface comprises a plurality of user selectable inputs corresponding to an image to display, the plurality of user selectable inputs comprising a first input to display the 3D view, a second input to display the sagittal view and a third input for the user to select one or more of the transverse images, for example.

In some embodiments, the plurality of transverse images corresponds to a plurality of predefined anatomical locations of an organ. In some embodiments, the plurality of predefined anatomical locations comprises anatomical locations of first organ and a second organ in which the first organ and the second organ are visible in the one or more longitudinal images and one or more of the transverse images. In some embodiments, wherein the first organ comprises a prostate and the second organ comprises a bladder, for example. In some embodiments, the plurality of predefined anatomical locations comprises an intravesical prostatic protrusion (IPP), a bladder neck (BL), the a prostate (MID), a verumontanum (VERU), and a peripheral sphincter (P. SPH).

At a step 1045, the received images are processed with an AI algorithm. The AI algorithm can be configured to identify one or more tissue structures as described herein. The AI algorithm may comprise one or more of image enhancement, image segmentation, a neural network, a convolutional neural network, a transformer, a transformer machine learning model, supervised machine learning, unsupervised machine learning, edge detection, feature recognition, segmentation, 3D model reconstruction, or a multi-modality image fusion, for example. The locations of the one or more tissue structures in the images can be used to identify images to show to the user, such as one or more transverse images corresponding to a location of a tissue structure. In some embodiments, the plurality of predefined anatomical locations has been identified with an artificial intelligence algorithm. In some embodiments, the AI algorithm is configured to process the received images and identify images corresponding to the predefined anatomical locations, and the selected images presented to the user in response to the identified locations and corresponding images. In some embodiments, the plurality of predefined anatomical locations comprises an intravesical prostatic protrusion (IPP), a bladder neck (BL), the a prostate (MID), a verumontanum (VERU), and a peripheral sphincter (P. SPH), and the transverse images shown to the user are based on the anatomical locations identified by the AI algorithm.

At a step 1050, a treatment profile is generated, and the treatment profile can be generated in any way as described herein. In some embodiments, the treatment profile comprises a 3D treatment profile.

At a step 1060, the treatment profile is overlaid on the one or more images. In some embodiments, the one or more images comprise one or more selected images, in which the images have been selected in response to user input, for example. In some embodiments, the representation of the 3D treatment profile comprises a three dimensional (3D) treatment volume overlaid on the arrangement of images shown in the 3D view. In some embodiments, the 3D treatment volume extends along the one or more longitudinal images in a longitudinal direction and along one or more transverse images in a direction transverse to the one or more longitudinal images. In some embodiments, an outer boundary of the 3D treatment volume is shown extending along the one or more longitudinal images transverse to the one or more longitudinal images and along the transverse image in the longitudinal direction.

In some embodiments, a representation of a 3D treatment profile in the 3D view comprises an intersection of the 3D treatment profile with the one or more longitudinal images and one or more of the plurality of transverse images.

In some embodiments, the plurality of transverse images comprises a first portion on a first side of the one or more longitudinal images and a second portion on a second side of the one or more longitudinal images, in which the arrangement has a first portion in front of the one or more longitudinal images and the second portion behind the one or more longitudinal images in the 3D view. In some embodiments, the representation of the 3D treatment profile is overlaid in the 3D view on the first portion and the one or more longitudinal images, with the 3D representation extending along the first portion and the one or more longitudinal images from a common location where the first portion intersects the one or more longitudinal images. In some embodiments, the transverse view comprises sufficient transparency to view the 3D representation of the treatment profile on the second portion of the second portion of one or more of the transverse images. In some embodiments, the user interface is configured to display the treatment profile as a plurality of lines along the transverse image, which are connected with one or more lines along the one or more longitudinal images. In some embodiments, the 3D representation is shown as a mesh overlaid on the one or more images, for example. In some embodiments, the images shown in the 3D view are user selectable while the 3D representation is shown in the 3D view. In some embodiments, the user interface is configured for the user to select which images are shown in the 3D view, such that the user can select none of the images or a plurality of images overlaid with the 3D representation of the treatment profile, for example.

In some embodiments, the user interface is configured to adjust the 3D view with the treatment profile overlaid on the 3D view. In some embodiments, the arrangement of images comprises a 3D arrangement and the user interface is configured for the user to one or more of zoom, pan or rotate the 3D arrangement in the 3D view, and the treatment profile is correspondingly adjusted in the 3D view with the input to one or more of zoom, pan or rotate the 3D arrangement. In some embodiments, the representation of the 3D treatment profile moves with the 3D arrangement to maintain registration of the 3D treatment profile with the 3D arrangement in response to the user input to one or more of zoom, pan or rotate the 3D representation. In some embodiments, a representation of a treatment probe is shown extending along the one or more longitudinal images and the representation of the treatment probe moves with the 3D arrangement and the 3D treatment profile to maintain registration of the representation of the treatment probe with the 3D arrangement and the 3D treatment profile.

In some embodiments, the user input is configured to rotate the one or more longitudinal images and the plurality of transverse images from a first orientation to a second orientation. The first orientation shows a first portion of the plurality of transverse images and the 3D treatment profile in front of the one or more longitudinal images and a second portion of the plurality of transverse images and the 3D treatment profile behind the one or more longitudinal images. The second orientation shows the second portion of the plurality of transverse images and the 3D treatment profile in front of the one or more longitudinal images and the first portion of the transverse images and the 3D treatment profile behind the one or more longitudinal images.

At a step 1070, user input is received to adjust treatment profile. In some embodiments, the user interface is configured to receive a user input to adjust the one or more images, for example by moving a boundary of the treatment profile as described herein.

At a step 1080, the adjusted treatment profile is shown on the display of the user interface. In some embodiments, the adjusted treatment profile is shown with a real time update to the treatment profile shown in the view that the user is adjusting, and with a real time update to additional views as described herein.

At a step 1090, a user input is received for the user to accept of the adjusted treatment profile. The user input to accept the treatment may comprise a user input that is received in advance of treatment. Also, the user input as described herein may comprise a user input from a first user and a user input from a second user. Alternatively, the user inputs may comprise inputs from a single user, for example.

At a step 1095, the patient is treated. The treatment can be performed in a substantially automated matter, for example with the user pressing a foot pedal or other device, once the user has accepted the treatment.

Although a method 1000 of planning a treatment is shown and described in accordance with some embodiments, one of ordinary skill in the art will recognize many adaptations and variations in accordance with the present disclosure. For example, the steps can be performed in any order. Some of the steps repeated, and some of the steps omitted. Some of the steps may comprise substeps of other steps. Also, one or more of the steps of method 1000 can be combined with any step of any method described herein.

FIG. 11 shows a method 1100 of planning a 3D treatment with automated tissue recognition.

At a step 1101 a plurality of images is received. The plurality of images may comprise any suitable images as described herein, such as a plurality of transverse images, one or more longitudinal images, or images of a 3D volumetric image such as a 3D ultrasound image, and combinations thereof. In some embodiments each of a plurality of images is received and evaluated, and the probe location and tissue boundaries determined in each of the plurality of images to generate the 3D treatment plan. The following steps may be performed on each of the plurality of images.

At a step 1103, the received images are processed with an AI algorithm. The AI algorithm can be configured to identify tissue structures that are used for treatment planning as described herein. In some embodiments, the AI algorithm is configured to identify the position of the probe in the plurality of images. The plurality of images may comprise any suitable images as described herein, such as transverse images, one or more longitudinal images, or images from a 3D volumetric image, and combinations thereof. The AI algorithm may comprise one or more of image enhancement, image segmentation, a neural network, a convolutional neural network, a transformer, a transformer machine learning model, supervised machine learning, unsupervised machine learning, edge detection, feature recognition, segmentation, 3D model reconstruction, or a multi-modality image fusion, for example.

At a step 1105, a treatment probe position is determined. The probe position may comprise an elongate axis of the probe, which may correspond to a position of an energy source during treatment. In some embodiments, the energy source may not be offset from the elongate axis during treatment, and the treatment plan and angles and distances determined in response to the position of the energy source during treatment. In some embodiments, the position of the probe is determined with an AI algorithm as described herein. Alternatively or in combination, a user interface can be configured for a user to identify the position of the probe.

At a step 1110, a tissue boundary is determined. In some embodiments, the boundary defines an area of the tissue to be treated. In some embodiments, the boundary of the tissue is determined with an AI algorithm as described herein. Alternatively or in combination, a user interface can be configured for a user to identify the boundary.

In some embodiments, the boundary encloses the anatomical tissue structure and may comprise a perimeter around the anatomical tissue structure in said each of the plurality of transverse images, and parameters of the boundary in relation to the probe used to plan the treatment. In some embodiments, the boundary comprises a margin with respect to the treatment probe. In some embodiments, a first margin of the tissue boundary corresponds to a first line from the probe to a first location of the boundary that is tangential to the boundary at the first location and a second margin of the tissue boundary corresponds to a second line from the probe that is tangential to the boundary at the second location of the boundary.

In some embodiments, the boundary of the tissue is separated from the probe by a distance, and the distances and angles between the tissue boundary can be used as input to determine the treatment profile and plan. In some embodiments, the probe is separated from the boundary by a closest distance at a location of the boundary closest to the probe and by a farthest distance at a location of the boundary farthest from the probe.

At a step 1115, a tissue profile is determined. In some embodiments, the tissue profile comprises a variable thickness between the first angle of the boundary and the second angle of the boundary. In some embodiments, the variable thickness tissue profile comprises a plurality of depths at a plurality of angles. In some embodiments, the tissue profile is separated from the probe with a gap between the probe and the treatment tissue profile. In some embodiments, the tissue profile comprises a plurality of first radial distances from the probe to a first portion of the boundary at a plurality of corresponding angles, and a second plurality of radial distances from the probe to a second portion of the boundary. In some embodiments, the first portion of the boundary is oriented toward the probe, and the second portion of the boundary is oriented away from the treatment probe. In some embodiments, the variable thickness profile of the tissue is defined by differences between the first plurality of radial distances and the second plurality of radial distances at the corresponding angles.

At a step 1120, angles of treatment are determined. In some embodiments, a first angle from the treatment probe to a first location along the boundary on a first side of the area and a second angle from the treatment probe to a second location along the boundary on a second side of the area are determined.

In some embodiments, the treatment plan is configured to provide one or more tissue margins. In some embodiments, the first treatment angle is oriented to provide a first tissue margin on the first side and the second treatment angle is oriented to provide a second tissue margin on the second side of the treated tissue. In some embodiments, the first treatment angle is selected to provide a first tissue margin thickness at the first treatment angle greater than a penetration depth of the energy source at the first treatment angle, and the second treatment angle is selected to provide a second tissue margin thickness at the second treatment angle greater than a depth of penetration of the energy source at the second treatment angle. In some embodiments, the first tissue margin corresponds to a first tissue margin angle between the first treatment angle and a first angle of a first margin of the boundary on the first side of the treated tissue, and the second tissue margin corresponds to a second tissue margin angle between the second treatment angle and a second angle of a second margin of the boundary on the second side of the tissue to be treated.

In some embodiments, the first tissue margin angle is within a range from about 1 degree to about 15 degrees and optionally within a range from about 1 degree to about 10 degrees and further optionally within a range from about 2 degrees to about 10 degrees. In some embodiments, the second tissue margin angle is within a range from about 1 degree to about 15 degrees and optionally within a range from about 1 degree to about 10 degrees and further optionally within a range from about 2 degrees to about 10 degrees.

In some embodiments, the treatment plan corresponds to a first depth of penetration of the energy source at the first treatment angle and the first tissue margin comprises a first tissue margin thickness at the first treatment angle, in which the first margin thickness is greater than the first depth of tissue penetration. In some embodiments, the first margin thickness is greater than the first penetration depth by an amount within a range from about 1 percent to about 15 percent and optionally within a range from about 1 percent to about 10 percent and further optionally within a range from about 2 percent to about 10 percent. In some embodiments, the treatment plan corresponds to a second depth of penetration of the energy source at the second treatment angle, and the second tissue margin comprises a second tissue margin thickness at the second treatment angle, in which the second margin thickness is greater than the second depth of tissue penetration. In some embodiments, the second margin thickness is greater than the second penetration depth by an amount within a range from about 1 percent to about 15 percent and optionally within a range from about 1 percent to about 10 percent and further optionally within a range from about 2 percent to about 10 percent.

In some embodiments, the first treatment angle is determined in response to a first boundary angle between the treatment probe and the boundary of the tissue on the first side and the second treatment angle is determined in response to a second boundary angle between the treatment probe and the boundary of the tissue on the second side. In some embodiments, the first treatment angle and the first boundary angle are arranged to provide a first tissue margin between the first treatment angle and the first boundary angle, and the second treatment angle and the second boundary angle are arranged to provide a second tissue margin between the second treatment angle and the second boundary angle. In some embodiments, the first boundary angle is determined from a first angle of the treatment probe to a first margin of the boundary on the first side and the second boundary angle is determined from a second angle from the treatment probe to a second margin of the boundary on the second side. In some embodiments, the first boundary angle corresponds to a first projection line from the probe to a first boundary location that is tangential to the boundary on the first side, and the second boundary angle corresponds to a second projection line from the probe that is tangential to the boundary on the second side. In some embodiments, the first tissue margin extends between the first margin of the boundary and the first treatment location at the first treatment angle on the first side and the second tissue margin extends between the second margin of the boundary and the second treatment location at the second treatment angle on the second side.

At a step 1125, removal layers are determined. In some embodiments, the removal layers are determined in order to provide a treatment with more than one sweep of the energy source across the tissue.

At a step 1130, layer boundaries are determined. In some embodiments, the boundaries of the removal layers are determined to provide one or more tissue margins as described herein.

At a step 1140, a treatment profile is generated for each of the plurality of images.

In some embodiments, the treatment profile comprises a variable thickness between the first angle on the first side of the treatment and the second angle on the second side of the treatment area and may comprise a plurality of depths at a plurality of corresponding angles. In some embodiments, the treatment profile is separated from the probe with a gap between the probe and the treatment profile. In some embodiments, the treatment profile comprises a plurality of thicknesses corresponding to a plurality of rotation angles of an energy source and each of the plurality of thicknesses is determined for a corresponding angle of the plurality of rotation angles. In some embodiments, each of the plurality of thicknesses comprises a distance between a first location of the tissue boundary and a second location of the tissue boundary at the corresponding angle. In some embodiments, for each of the plurality of thicknesses of the treatment profile, the first location is separated from the probe by a first distance and the second location is separated from the probe by a second distance.

At a step 1145, a 3D treatment profile is generated. In some embodiments, the 3D treatment profile is generated from the plurality of 2D treatment profiles. Alternatively, the 3D treatment profile can be generated from a 3D tissue profile, in which the 3D treatment tissue profile has been generated from the boundaries of the tissue profiles in the plurality of images.

At a step 1150, a 3D treatment plan is generated. In some embodiments, the 3D treatment plan is generated for each of the plurality of images and combined. The 3D treatment plan can be generated from the tissue boundaries, or from treatment profiles determined from the tissue boundaries, and combinations thereof. Alternatively or in combination, the 3D treatment plan can be generated from a 3D tissue profile. In some embodiments, the 3D treatment plan is generated from a 3D treatment profile.

In some embodiments, the treatment plan is generated in response to a first angle and a second angle of the probe with respect to the tissue boundary for each of the plurality of transverse images. In some embodiments, the location of the probe corresponds to a location of a directional energy source during treatment, and the first angle corresponds to a first angle of the directional energy source during treatment and the second angle corresponds to a second angle of the energy source during treatment. In some embodiments, the first angle and the second angle of said each of the plurality of transverse images corresponds to a plurality of treatment angles of the 3D treatment plan. For example, the first angle and the second and from said each the plurality of transverse images are combined to generate the 3D treatment plan.

In some embodiments, the plurality of transverse images is located along a treatment axis corresponding to axial translation of a directional energy source on the probe during treatment and each of the plurality of transverse images is located at a position along the treatment axis. In some embodiments, the treatment plan is configured to rotate the probe to direct energy from an energy source at the first angle to the first location and at the second angle to the second location for each of the plurality of locations along the treatment axis. In some embodiments, the treatment plan is configured to rotate the energy source from the first angle to the second angle to scan the energy source across the tissue between the first angle and the second angle.

In some embodiments, the treatment plan comprises machine readable instructions to move the probe to a plurality of axial locations along a treatment probe axis and to rotate the probe to a plurality of angles to deliver energy from an energy source at the plurality of axial locations and the plurality of angles. In some embodiments, the treatment plan comprises a first angle and a second angle for each of the plurality of locations and is configured to scan the energy source along the tissue between the first angle and the second angle at said each of the plurality of axial locations.

In some embodiments, the treatment plan is configured to treat tissue in accordance with a treatment profile corresponding to the boundary of the tissue. In some embodiments, the boundary comprises a boundary of an anatomical tissue structure separated from the probe by a distance. In some embodiments, the treatment plan is configured to adjust delivery of the energy from the energy source in response to the distance. In some embodiments, the directional energy source comprises an increasing cross-sectional area at distances away from the energy source, and the distance can be used to adjust energy delivered from the energy source as described herein.

In some embodiments, the treatment plan is configured to remove tissue at a plurality of thicknesses at a plurality of corresponding angles between the first angle and the second angle. In some embodiments, the treatment plan is configured to remove tissue to a first depth with a first pass of the energy source at a first angular subsense between the first angle and the second angle and to remove tissue to a second depth with a second pass of the energy source corresponding to a second angular subtense less than the first angular subsense, the second depth greater than the first depth. In some embodiments, the second angular subtense corresponds to a third location along the boundary on the first side of the area and a fourth location along the boundary on the second side of the area. In some embodiments, the third location of the boundary is located at or below the first removal depth and the fourth location of the boundary is located at or below the first removal depth.

In some embodiments, each of the plurality of thicknesses comprises a distance from a proximal location of the boundary to a distal location of the boundary for an angle of the plurality of corresponding angles.

While the treatment can be performed in many ways, in some embodiments the treatment plan is configured to adjust one or more of an intensity of energy from the energy source, a power of energy from the energy source, translational velocity of the energy source, a rotational velocity of the energy source, or a number of passes of the energy source at the plurality of corresponding angles to treat the tissue in accordance with the plurality of thicknesses. In some embodiments, the treatment plan is configured to fix an axial position of the treatment probe and rotate the treatment probe at the axial position to scan energy from the energy source along the tissue with a first pass between first angles and a second pass between second angles at the axial position. Alternatively or in combination, the treatment plan may be configured to fix a rotational angle of the treatment probe about the elongate probe axis and translate the treatment probe at the rotational angle to scan energy from the energy source along the tissue with a first pass between first translational locations and a second pass between second translational location at the rotational angle, for example. In some embodiments, the treatment plan is configured to increase a translational velocity of the energy source on the treatment probe to decrease a treatment depth and decrease the translational velocity to increase the treatment depth. Alternatively or in combination, the treatment plan may be configured to increase a rotational velocity of the energy source on the treatment probe to decrease a treatment depth and decrease the rotational velocity to increase the treatment depth, for example.

At a step 1165, images are presented to the user with treatment profile overlaid on the images. The presented images may comprise any image or view as described herein. This can be helpful for the user to evaluate and verify the treatment plan. For example, with AI based treatment planning, it can be helpful to have a person review the treatment plan prior to treating the patient.

At a step 1167, user input is received to adjust the treatment profiles. This can be helpful if the user would like to make changes to the treatment plan. The treatment profile can be adjusted in any way as described herein.

At a step 1170, a second tissue boundary is determined. In some embodiments, the second tissue comprises a non-treated tissue, although the second tissue may comprise a second treated tissue, for example. In some embodiments, the boundary of the second tissue is determined with an AI algorithm as described herein. In some embodiments, the first tissue comprises a first anatomical tissue structure and the second tissue comprises a second anatomical tissue structure different from the first anatomical tissue structure. the first anatomical tissue structure comprises an anatomical tissue structure of a first organ and the second anatomical tissue structure comprises a second anatomical tissue structure of a second organ different from the first organ.

In some embodiments, the anatomical structure of the first tissue structure comprises one or more of a tissue wall, a vesicle, a lumen, a wall of a lumen, a bladder, a wall of a bladder, a neck of a bladder, a wall of a bladder neck, a ureteric orifice, an internal urethral orifice, an external urethral sphincter, a ureter, a wall of a ureter, a prostate, a lobe of a prostate, an intravesical prostatic protrusion, a capsule of a prostate, an internal sphincter, and external sphincter, an artery, a wall of an artery, a vein, a wall of a vein, or a lens of an eye, for example. The second tissue structure may comprise any suitable tissue, such as one or more connective tissue, muscle tissue, epithelial tissue, muscle tissue, or an anatomical structure associated with a contrast in the image data.

In some embodiments, the second tissue structure comprises a second type of tissue adjacent a third type of tissue or a fluid to provide the contrast in the image data from the second tissue structure. The fluid may comprise a liquid such as urine, for example.

In some embodiments, the anatomical structure of the second tissue structure comprises one or more of a tissue wall, a vesicle, a lumen, a wall of a lumen, a bladder, a wall of a bladder, a neck of a bladder, a wall of a bladder neck, a trigone tissue, a ureteric orifice, an internal urethral orifice, an external urethral sphincter, a ureter, a wall of a ureter, a prostate, a lobe of a prostate, an intravesical prostatic protrusion, a capsule of a prostate, a verumontanum of a prostate, an internal sphincter, and external sphincter, an artery, a wall of an artery, a vein, a wall of a vein, or a retina of an eye, for example.

At a step 1180, the second tissue boundary is compared to the treatment plan. This comparison may include a comparison of angles and distances of the second tissue to the probe, for example. In some embodiments, the comparison is made with respect to the boundary of the first tissue, for example to determine if the first tissue is located between the energy source and the second tissue. In some embodiments, the distance between the boundary of the first tissue and the boundary of the second tissue are compared, to determine whether there is sufficient distance between the first tissue boundary and the second tissue boundary, for example.

At a step 1185, an output to the user interface is generated. While the output can be configured in many ways, in some embodiments output comprises feedback to a user generated in response to the comparison at step 1180, and the feedback may comprise one or more of a notification or an alert to the user. In some embodiments, the boundary of the first tissue is located between the boundary of the second tissue and the output is generated in response to a distance between the probe and the location of the second tissue boundary, for example. In some embodiments, the treatment plan comprises an angle of rotation of an energy source beyond a margin of the boundary of the first tissue and the output is generated in response to the angle of rotation beyond the margin. In some embodiments, the treatment plan corresponds to a depth of penetration of an energy source beyond a thickness of the tissue and the output is generated in response to the depth of penetration greater than the thickness. In some embodiments, the thickness comprises a plurality of thicknesses at a plurality of rotation angles of an energy source, in which each of the plurality of thicknesses is determined for a corresponding angle of the plurality of rotation angles, and a penetration depth is determined for each of the plurality of angles. The output can be generated in response to a penetration depth exceeding the thickness of the tissue, for example.

Although reference is made to an output such as a notification or an alert, in some embodiments the boundary of the first tissue, the boundary of the second tissue, and a treatment profile are shown in one or more views of the images and the user interface is configured to adjust the treatment plan, for example by moving the treatment profile as described herein. In some embodiments, the boundary of the first tissue, the boundary of the second tissue, and a treatment profile are shown on each of the plurality of transverse images and the user interface is configured to adjust the treatment profile on the plurality of transverse images, for example.

At a step 1190, an input from the user interface is received. The input may comprise any suitable input as describe herein, such as an input to modify the treatment profile. In some embodiments, the input comprises an input indicating that the user accepts the treatment plan such as a treatment profile.

At a step 1195, the patient is treated.

Although a method 1100 of planning a 3D treatment with automated tissue recognition is shown and described in accordance with some embodiments, one of ordinary skill in the art will recognize many adaptations and variations in accordance with the present disclosure. For example, the steps can be performed in any order. Some of the steps repeated, and some of the steps omitted. Some of the steps may comprise substeps of other steps. Also, one or more of the steps of method 1100 can be combined with any step of any method described herein.

FIG. 12 shows a method 1200 of treating a first tissue and decreasing exposure to a second tissue with automated tissue recognition.

At a step 1210, an AI algorithm detects a first tissue such as an IPP of the prostate and a second tissue such as a trigon tissue of bladder. The AI algorithm may comprise one or more of image enhancement, image segmentation, a neural network, a convolutional neural network, a transformer, a transformer machine learning model, supervised machine learning, unsupervised machine learning, edge detection, feature recognition, segmentation, 3D model reconstruction, or a multi-modality image fusion, for example.

At a step 1220, an AI algorithm detects the first tissue and the second tissue in a plurality of transverse images.

At a step 1230, an AI algorithm measures the distance from the energy source such as a nozzle to the second tissue such as the IPP and angles of the IPP in the plurality of transverse images.

At a step 1240, the AI algorithm generates an output such as a warning indicating that the first tissue such as the IPP may have a penetration depth that exceeds the tissue thickness or a treatment angle outside the angles of the first tissue such as the IPP.

At a step 1250, the AI algorithm determines the boundary of the first tissue such as the IPP and evaluates whether the treatment plan exceeds energy deliver that is sufficient for the treatment of the first tissue. For example, the AI algorithm can be configured to determine whether the penetration depth of the energy source exceeds the thickness of the first tissue. In some embodiments, the AI algorithm is configured to determine whether the translational positions of the energy source during treatment extends beyond the first tissue so as to imping on the second tissue, such as the IPP, for example.

At a step 1260, the treatment plan is adjusted. While the treatment plan can be adjusted in many ways, in some embodiments the treatment profile is adjusted to limit the treatment to the first tissue, for example with an adjustment to one or more of treatment angles to appropriately limit the treatment angles, or with an adjustment to the depth of penetration of the tissue so as to limit the depth of penetration to the thickness of the tissue.

Although a method 1200 of planning a treatment is shown and described in accordance with some embodiments, one of ordinary skill in the art will recognize many adaptations and variations in accordance with the present disclosure. For example, the steps can be performed in any order. Some of the steps repeated, and some of the steps omitted. Some of the steps may comprise substeps of other steps. Also, one or more of the steps of method 1200 can be combined with any step of any method described herein.

FIG. 13 shows a method 1300 of training an AI algorithm.

At a step 1310, images are collected and grouped. The images may comprise a collection of images acquired prior to and during treatment. The images can be appropriately classified and grouped, for example classified and grouped with respect to a type of tissue. In some embodiments, the images are group according to a type of tissue, such as types of prostate tissue as described herein, for example.

At a step 1320, the AI model receives the grouped images from step 1310. The machine assisted labeling (MAL) is used to is used to label the grouped images in accordance with each group of the images. In some embodiments, each group of images may be segmented and classified and labeled with a MAL. In some embodiments, the images are segmented and annotated with labels so as to identify tissue structures as described herein, for example.

At a step 1330, the MAL images are received by a user interface that allows an expert to review and cleanup of the MAL image data. The initial set of MAL images may be reviewed an expert such as a radiologist, for example. The expert review and cleanup of the MAL images generates high quality labeled image data. The high quality labeled image data can be added to a pool of high quality image data. This high quality image data can be used as a ground state or truth state to further train and refine the classifier and contains annotated data with appropriate labels identifying the type of tissue.

At a step 1340, the high quality labeled data is received by an AI algorithm as described herein and used for training and validation of the model. The annotated images can be used to train and validate the AI algorithm and develop model parameters of the AI algorithm. The AI algorithm may comprise any suitable algorithm as described herein, such as a neural network, e.g. a deep neural network for example.

At a step 1350, the trained model parameters generated at step 1340 are received to refine and tune the model. While this can be performed in many ways, in some embodiments model inference speed improvements are performed on the model to increase the speed of the model without substantially compromising the output of the model. This can be helpful to increase throughput of the model and decrease processing bottle necks in the model.

At a step 1360, the model is released and deployed in the field. This field deployed model can be used to process images to generate one or more tissue structures as described herein.

In some embodiments, the model is further refined prior to the field deployment at step 1360. For example, it can be helpful to iterate and refine the model by repeating steps 1320, 1330, 1340 and 1350 to generate acceptable model parameters for field deployment at step 1360. In some embodiments, steps 1320, 1330, 1340 and 1350 comprise elements of a feedback loop. In some embodiments, the new model parameters developed at step 1350 are provided to the grouped images for MAL at step 1320 and then MAL images provided to the expert for review at step 1330. In some embodiments, additional images are provided for testing and validation at step 1320 and MAL images generated and provided to the expert for review at step 1330, and these images added to the pool of image data. In some embodiments, the new model parameters generated at step 1350 can be provided to the AI algorithm at step 1340 and used to evaluate the images and used to further refine and develop the AI algorithm at step 1340. Once the AI algorithm training and development has been completed at step 1340, this trained model can be refined at step 1350 for model inference speed improvement, for example. The steps, 1320,

1330, 1340 and 1350 can be performed as many times as appropriate to further refine and improve the model prior to field deployment at step 1360.

Although a method 1300 of training an AI algorithm is shown and described in accordance with some embodiments, one of ordinary skill in the art will recognize many adaptations and variations in accordance with the present disclosure. For example, the steps can be performed in any order. Some of the steps repeated, and some of the steps omitted. Some of the steps may comprise substeps of other steps. Also, one or more of the steps of method 1300 can be combined with any step of any method described herein.

The processor as described herein can be configured to perform one or more steps of any method disclosed herein, such as method 1000, method 1100, method 1200 or method 1300, for example.

FIG. 14 shows an artificial intelligence ("AI") algorithm suitable for incorporation in accordance with embodiments of the present disclosure. In some embodiments, the artificial intelligence algorithm comprises one or more of image enhancement, image segmentation, a neural network, a convolutional neural network, a transformer, a transformer machine learning model, supervised machine learning, unsupervised machine learning, edge detection, feature recognition, segmentation, 3D model reconstruction, or a multi-modality image fusion, for example.

In some embodiments, the AI algorithm comprises a two-dimensional convolutional neural network (CNN) 2100. In some embodiments, the AI such as a CNN is configured to identify one or more tissue structures of one or more tissue and process the images identify the tissue structure and determine a response of the tissue to treatment. The tissue may comprise a first tissue, or a second tissue, or combinations thereof as described herein. A dataset 2102 is initially provided, which may include imagery from historical treatment data from prior patients and procedures. A convolution operation 2104 results in data in a 2nd data set 2106, which in turn has a pooling layer 2108 applied to result in a pooled layer 2110 of subsample data in order to further condense the spatial size of the representation. The subsample data may be convoluted 2112 to produce a third data set 2114, which may further have a pooling layer applied 2116 to provide subsample data 2118. The subsample data 2118 may be passed through a first fully connected layer 2120 and a second fully connected layer 2122 to generate a classification matrix output 2124. One or more filters can be applied at each convolution layer to provide different types of feature extraction. After the model is defined, it may be compiled and may utilize accuracy of the feature recognition as a performance metric. The model may be trained over time, such as by using historical procedure data as training data and verified according to the model's predictions and verified over time until the model's predictions converge with truth data.

While the trained model can be configured in many ways, in some embodiments the trained model is configured to identify a tissue structure and output one or more metrics associated with the tissue structure, such as one or more of shape data or movement data as described herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of" Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein "e.g." means for example.

As used herein, characters such as numerals refer to like elements.

The present disclosure includes the following numbered clauses.

Clause 1. A method of planning a treatment, the method comprising: receiving a plurality of transverse images and one or more longitudinal images of a tissue; generating an arrangement of the plurality of transverse images along the one or more longitudinal images in a three-dimensional (3D) view, the three dimensional view comprising the plurality of transverse images at a plurality corresponding locations along the one or more longitudinal images; overlaying a representation of a three dimensional (3D) treatment profile on the 3D view of the plurality of transverse images and the one or more longitudinal images; and providing to a display of a user interface, the 3D view with the representation overlaid on the one or more longitudinal images and one or more of the plurality of transverse images.

Clause 2. The method of clause 1, wherein in the 3D view, the plurality of transverse images comprises a first portion on a first side of the one or more longitudinal images and a second portion on a second side of the one or more longitudinal images, the first portion in front of the one or more longitudinal images and the second portion behind one or more longitudinal images.

Clause 3. The method of any of clauses 1 to 2, wherein the representation of the 3D treatment profile is overlaid in the 3D view on the first portion and the one or more longitudinal images, with the 3D representation extending along the first portion and the one or more longitudinal images from a common location where the first portion intersects the one or more longitudinal images.

Clause 4. The method of any of clauses 1 to 3, wherein the one or more longitudinal images comprises an amount of transparency sufficient to view the second portion of one or more of the transverse images through the one or more longitudinal images.

Clause 5. The method of any of clauses 1 to 4, wherein the representation of the 3D treatment profile is overlaid on the second portion on the second side and the amount of transparency is sufficient to view the representation of the 3D treatment profile on the second side through the one or more longitudinal images.

Clause 6. The method of any of clauses 1 to 5, wherein the arrangement comprises a three dimensional (3D) arrangement and the user interface comprises an input for a user to one or more of zoom, pan or rotate the 3D arrangement in the 3D view.

Clause 7. The method of any of clauses 1 to 6, wherein the representation of the 3D treatment profile moves with the 3D arrangement to maintain registration of the 3D treatment profile with the 3D arrangement in response to the user input to one or more of zoom, pan or rotate the 3D representation.

Clause 8. The method of any of clauses 1 to 7, wherein the user input is configured to rotate the one or more longitudinal images and the plurality of transverse images from a first orientation to a second orientation, the first orientation showing a first portion of the plurality of transverse images in front of the one or more longitudinal images and a second portion of the plurality of transverse images behind the one or more longitudinal images, the second orientation showing the second portion of the plurality of transverse images in front of the one or more longitudinal images and the second portion of the transverse images behind the one or more longitudinal images.

Clause 9. The method of any of clauses 1 to 8, wherein a representation of a treatment probe is shown extending along the one or more longitudinal images and the representation of the treatment probe moves with the 3D arrangement and the 3D treatment profile to maintain registration of the representation of the treatment probe with the 3D arrangement and the 3D treatment profile.

Clause 10. The method of any of clauses 1 to 9, wherein the representation of the 3D treatment profile comprises a three dimensional (3D) treatment volume overlaid on the arrangement.

Clause 11. The method of any of clauses 1 to 10, wherein the 3D treatment volume extends along the one or more longitudinal images in a longitudinal direction and along one or more transverse images in a direction transverse to the one or more longitudinal images.

Clause 12. The method of any of clauses 1 to 11, wherein an outer boundary of the 3D treatment volume is shown extending along the one or more longitudinal images transverse to the one or more longitudinal images and along the transverse image in the longitudinal direction.

Clause 13. The method of any of clauses 1 to 12, wherein a representation of a treatment probe is shown in the 3D view extending in a longitudinal direction.

Clause 14. The method of any of clauses 1 to 13, wherein the representation comprises an animation of the treatment probe.

Clause 15. The method of any of clauses 1 to 14, wherein the animation of the treatment probe is configured to move to show an animation of the treatment probe delivering energy from an energy source in accordance with a 3D treatment plan.

Clause 16. The method of any of clauses 1 to 15, wherein the representation comprises an image of the treatment probe from an imaging device.

Clause 17. The method of any of clauses 1 to 16, wherein a representation of a 3D treatment profile in the 3D view comprises an intersection of the 3D treatment profile with the one or more longitudinal images and one or more of the plurality of transverse images.

Clause 18. The method of any of clauses 1 to 17, wherein the plurality of transverse images corresponds to a plurality of predefined anatomical locations of an organ.

Clause 19. The method of any of clauses 1 to 18, wherein the plurality of predefined anatomical locations comprises anatomical locations of first organ and a second organ in which the first organ and the second organ are visible in the one or more longitudinal images and one or more of the transverse images.

Clause 20. The method of any of clauses 1 to 20, wherein the plurality of predefined anatomical locations has been identified with an artificial intelligence algorithm.

Clause 21. The method of any of clauses 1 to 20, wherein the first organ comprises a prostate and the second organ comprises a bladder.

Clause 22. The method of any of clauses 1 to 21, wherein the plurality of predefined anatomical locations comprises an intravesical prostatic protrusion (IPP), a bladder neck (BL), the a prostate (MID), a verumontanum (VERU), and a peripheral sphincter (P. SPH).

Clause 23. The method of any of clauses 1 to 22, wherein the user interface is configured to receive a user input identifying a selected image among the one or more longitudinal images and the plurality of transverse images shown in the 3D view and display the selected image with a 2D view.

Clause 24. The method of any of clauses 1 to 23, wherein the user input corresponds to a location of the selected image in the 3D view and a user input at the location with a pointing device or a touch screen display.

Clause 25. The method of any of clauses 1 to 24, wherein the user interface comprises a plurality of user selectable inputs corresponding to an image to display, the plurality of user selectable inputs comprising a first input to display the 3D view, a second input to display the one or more longitudinal images and a third input for the user to select one or more of the transverse images.

Clause 26. The method of any of clauses 1 to 25, wherein the user interface is configured to receive a user input selecting a transverse image among the plurality of transverse images and provide a two dimensional (2D) view of the transverse image with the representation overlaid on the 2D view of the transverse image in response to the user input.

Clause 27. The method of any of clauses 1 to 26, wherein the user interface is configured to receive a user input selecting the one or more longitudinal images and provide a 2D view of the one or more longitudinal images with the representation overlaid on the 2D view of the one or more longitudinal images in response to the user input.

Clause 28. The method of any of clauses 1 to 27, wherein the plurality of transverse images intersects the one or more longitudinal images at the plurality of corresponding locations.

Clause 29. The method of any of clauses 1 to 28, wherein the plurality of transverse images comprises volumetric pixels (voxels) overlapping with the one or more longitudinal images at the plurality of corresponding locations.

Clause 30. The method of any of clauses 1 to 29, wherein each of the plurality of transverse images appears substantially perpendicular to the one or more longitudinal images in the 3D view and optionally to within five degrees of perpendicular.

Clause 31. The method of any of clauses 1 to 30, wherein the 3D view comprises a perspective view of the plurality of transverse images and the one or more longitudinal images.

Clause 32. The method of any of clauses 1 to 31, wherein the plurality of transverse images and the one or more longitudinal images comprise images from a 3D tomographic image.

Clause 33. The method of any of clauses 1 to 32, wherein the plurality of transverse images and the one or more longitudinal images comprise ultrasound images and optionally wherein the ultrasound images comprise images from an ultrasound probe inserted into the patient.

Clause 34. The method of any of clauses 1 to 33, wherein the one or more longitudinal images comprises a plurality of longitudinal images.

Clause 35. The method of any of clauses 1 to 34, wherein the plurality of longitudinal images has been generated from a 3D volumetric image of the tissue.

Clause 36. The method of any of clauses 1 to 35, wherein the plurality of longitudinal images has been generated in response to a plurality of angles of an energy source to treat the tissue.

Clause 37. The method of any of clauses 1 to 36, wherein the plurality of longitudinal images comprises a first longitudinal image along a first portion of the treatment profile and a second longitudinal image along a second portion of the treatment profile.

Clause 38. The method of any of clauses 1 to 37, wherein the arrangement shows a portion of the first longitudinal image along the first portion of the treatment profile and a portion of the second longitudinal image along the second portion of the treatment profile.

Clause 39. The method of any of clauses 1 to 38, wherein the first longitudinal image comprises a first transparency along the first portion of the treatment profile and a second transparency along the second portion of the treatment profile greater than the first transparency to increase visibility of the second longitudinal image along the second portion.

Clause 40. The method of any of clauses 1 to 39, wherein the second longitudinal image comprises a first transparency along the first portion of the treatment profile and a second transparency the second portion of the treatment profile, the first transparency greater than the second transparency to increase visibility of the first longitudinal image along the first portion of the treatment profile.

Clause 41. The method of any of clauses 1 to 40, wherein the plurality of longitudinal images comprises a first longitudinal image at a first angle with respect to an axis of rotation and a second longitudinal image at a second angle with respect the axis of translation.

Clause 42. The method of any of clauses 1 to 41, wherein the first angle corresponds to a first angle of rotation of an energy source about the axis and the second angle corresponds to a second angle of rotation of an energy source and optionally wherein the first angle and the second angle correspond to angles of rotation of an energy source inserted into the patient.

Clause 43. The method of any of clauses 1 to 42, wherein the first longitudinal image extends along a first portion of the treatment profile at the first angle and the second portion of the longitudinal image extends along a second portion of the treatment profile at the second angle.

Clause 44. The method of any of clauses 1 to 43, wherein the plurality of longitudinal images comprises at least 3 longitudinal images, each at a different angle of rotation with respect to an elongate axis of a treatment probe.

Clause 45. A method of generating a treatment plan, the method comprising: receiving a plurality of transverse images of a tissue to be treated; for each of the plurality of transverse images, determining a position of a treatment probe and a boundary of the tissue, the boundary defining an area of the tissue; for each of the plurality of transverse images, determining a first treatment angle from the treatment probe to a first treatment location on a first side of the area in response to the boundary and a second treatment angle from the treatment probe to a second treatment location on a second side of the area in response to the boundary; and generating the treatment plan in response to the first treatment angle and the second treatment angle of said each of the plurality of transverse images.

Clause 46. The method of clause 45, wherein the first treatment angle is oriented to provide a first tissue margin on the first side and the second treatment angle is oriented to provide a second tissue margin on the second side.

Clause 47. The method of any of clauses 45 to 46, wherein the first treatment angle is selected to provide a first tissue margin thickness at the first treatment angle greater than a penetration depth of the energy source at the first angle and the second treatment angle is selected to provide a second tissue margin thickness at the second angle greater than a depth of penetration of the energy source at the second angle.

Clause 48. The method of any of clauses 45 to 47, wherein the first tissue margin corresponds to a first tissue margin angle between the first treatment angle and a first angle of a first margin of the boundary on the first side and the second tissue margin corresponds to a second tissue margin angle between the second treatment angle and a second angle of a second margin of the boundary on the second side.

Clause 49. The method of any of clauses 45 to 48, wherein the first tissue margin angle is within a range from about 1 degree to about 15 degrees and optionally within a range from about 1 degree to about 10 degrees and further optionally within a range from about 2 degrees to about 10 degrees.

Clause 50. The method of any of clauses 45 to 49, wherein the second tissue margin angle is within a range from about 1 degree to about 15 degrees and optionally within a range from about 1 degree to about 10 degrees and further optionally within a range from about 2 degrees to about 10 degrees.

Clause 51. The method of any of clauses 45 to 50, wherein the treatment plan corresponds to a first depth of penetration of the energy source at the first treatment angle and the first tissue margin comprises a first margin thickness at the first treatment angle, the first margin thickness greater than the first depth.

Clause 52. The method of any of clauses 45 to 51, wherein the first margin thickness is greater than the first penetration depth by an amount within a range from about 1 percent to about 15 percent and optionally within a range from about 1 percent to about 10 percent and further optionally within a range from about 2 percent to about 10 percent.

Clause 53. The method of any of clauses 45 to 52, wherein the treatment plan corresponds to a second depth of penetration of the energy source at the second treatment angle and the second tissue margin comprises a second margin thickness corresponds the first treatment angle, the second margin thickness greater than the second penetration depth.

Clause 54. The method of any of clauses 45 to 53, wherein the second margin thickness is greater than the second penetration depth by an amount within a range from about 1 percent to about 15 percent and optionally within a range from about 1 percent to about 10 percent and further optionally within a range from about 2 percent to about 10 percent.

Clause 55. The method of any of clauses 45 to 54, wherein the first treatment angle is determined in response to a first boundary angle between the treatment probe and the boundary of the tissue on the first side and the second treatment angle is determined in response to a second boundary angle between the treatment probe and the boundary of the tissue on the second side.

Clause 56. The method of any of clauses 45 to 55, wherein the first treatment angle and the first boundary angle are arranged to provide a first tissue margin between the first treatment angle and the first boundary angle and wherein the second treatment angle and the second boundary angle are arranged to provide a second tissue margin between the second angle and the second boundary angle.

Clause 57. The method of any of clauses 45 to 56, wherein the first boundary angle is determined from the treatment probe to a first margin of the boundary on the first side and the second boundary angle is determined from the treatment probe to a second margin of the boundary on the second side.

Clause 58. The method of any of clauses 45 to 57, wherein the first boundary angle corresponds to a first projection line from the probe to a first boundary location that is tangential to the boundary on the first side and the second margin of the tissue boundary corresponds to a second projection line from the probe that is tangential to the boundary on the second side.

Clause 59. The method of any of clauses 45 to 58, wherein the first tissue margin extends between the first margin of the boundary and the first treatment location on the first side and the second tissue margin extends between the second margin of the boundary and the second treatment location on the second side.

Clause 60. The method of any of clauses 45 to 59, wherein, for each of the plurality of transverse images, the treatment plan is configured to treat tissue in accordance with a treatment profile corresponding to the first treatment angle and the second treatment angle.

Clause 61. The method of any of clauses 45 to 60, wherein the treatment profile comprises a variable thickness between the first treatment angle and the second treatment angle.

Clause 62. The method of any of clauses 45 to 61, wherein the treatment profile comprises a substantially uniform thickness between the first treatment angle and the second treatment angle and optionally wherein the substantially uniform thickness is uniform to within 20 percent.

Clause 63. The method of any of clauses 45 to 62, wherein the treatment profile is separated from the probe with a gap between the probe and the treatment profile.

Clause 64. The method of any of clauses 45 to 63, wherein the variable thickness comprises a first thickness corresponding to the first treatment angle, a second thickness corresponding to the second treatment angle and a central thickness at an angle between the first angle and the second angle, the central thickness of the treatment profile greater than the first thickness and the second thickness.

Clause 65. The method of any of clauses 45 to 64, wherein the treatment plan is configured to treat the first thickness and the second thickness with a first scan of energy from the energy source between the first treatment angle and the second treatment angle and the central thickness with the first scan and a second scan of the energy from the energy source.

Clause 66. The method of any of clauses 45 to 65, wherein the first scan comprises a first rotational scan of the energy source between the first treatment angle and the second treatment angle, and the second scan comprises a second rotational scan of the energy source, the second rotational scan comprising an angle of rotation less than the first rotational scan.

Clause 67. The method of any of clauses 45 to 66, wherein the treatment plan is configured to remove tissue at a plurality of thicknesses at a plurality of corresponding angles between the first treatment angle and the second treatment angle.

Clause 68. The method of any of clauses 45 to 67, wherein the treatment plan is configured to remove tissue to a first depth with a first pass of the energy source at a first angular subtense between the first treatment angle and the second treatment angle and to remove tissue to a second depth with a second pass of the energy source corresponding to a second angular subtense less than the first angular subsense, the second depth greater than the first depth.

Clause 69. The method of any of clauses 45 to 68, wherein the second angular subtense corresponds to a third location on the first side of the area and a fourth location on the second side of the area.

Clause 70. The method of any of clauses 45 to 69, wherein the third location is located at or below the first removal depth and the fourth location is located at or below the first removal depth.

Clause 71. The method of any of clauses 45 to 70, wherein each of the plurality of thicknesses comprises a distance from a proximal location of the boundary to a distal location of the boundary for an angle of a plurality of corresponding treatment angles.

Clause 72. The method of any of clauses 45 to 71, wherein the treatment plan is configured to adjust one or more of an intensity of energy from the energy source, a power of energy from the energy source, translational velocity of the energy source, a rotational velocity of the energy source, or a number of passes of the energy source at the plurality of corresponding angles to treat the tissue in accordance with the plurality of thicknesses.

Clause 73. The method of any of clauses 45 to 72, wherein the treatment profile comprises a plurality of thicknesses corresponding to a plurality of rotation angles of an energy source and each of the plurality of thicknesses is determined for a corresponding treatment angle of the plurality of rotation angles.

Clause 74. The method of any of clauses 45 to 73, wherein the probe is separated from the boundary by a closest distance at a location of the boundary closest to the probe and by a farthest distance at a location of the boundary farthest from the probe.

Clause 75. The method of any of clauses 45 to 74, wherein the first location at the first treatment angle is separated from the probe by a first distance and the second location at the second treatment angle is separated from the probe by a second distance.

Clause 76. The method of any of clauses 45 to 75, wherein the boundary comprises a boundary of an anatomical tissue structure separated from the probe by a distance and the treatment plan is configured to adjust delivery of the energy from the energy source in response to the distance and the first treatment angle and the second angle from said each of the plurality of transverse images.

Clause 77. The method of any of clauses 45 to 76, wherein the boundary encloses the anatomical tissue structure and optionally comprises a perimeter around the anatomical tissue structure in said each of the plurality of transverse images.

Clause 78. The method of any of clauses 45 to 77, wherein the boundary is determined by an artificial intelligence algorithm for said each of the plurality of transverse images.

Clause 79. The method of any of clauses 45 to 78, wherein the location of the probe corresponds to a location of a directional energy source during treatment for said each of the plurality transverse images and the first angle corresponds to a first angle of the directional energy source during treatment and the second angle corresponds to a second angle of the energy source during treatment.

Clause 80. The method of any of clauses 45 to 79, wherein the first angle, the second angle of said each of the plurality of transverse images corresponds to a plurality of treatment angles of a three dimensional (3D) treatment plan.

Clause 81. The method of any of clauses 45 to 80, wherein the first angle and the second and from said each the plurality of transverse images are combined to generate the 3D treatment plan.

Clause 82. The method of any of clauses 45 to 81, wherein the plurality of transverse images is located along a treatment axis corresponding to axial translation of a directional energy source on the probe during treatment and said each of the plurality of transverse images is located at a position along the treatment axis.

Clause 83. The method of any of clauses 45 to 82, wherein the treatment plan is configured to rotate the probe to direct energy from an energy source at the first angle to the first location and at the second angle to the second location for said each of the plurality of locations along the treatment axis.

Clause 84. The method of any of clauses 45 to 83, wherein the treatment plan is configured to rotate the energy source from the first angle to the second angle to scan the energy source across the tissue between the first angle and the second angle.

Clause 85. The method of any of clauses 45 to 84, wherein the treatment plan comprises machine readable instructions to move the probe to a plurality of axial locations along a treatment probe axis and to rotate the probe to a plurality of angles to deliver energy from an energy source at the plurality of axial locations and the plurality of angles.

Clause 86. The method of any of clauses 45 to 85, wherein the treatment plan comprises the first angle and the second angle for each of the plurality of locations and is configured to scan the energy source along the tissue between the first angle and the second angle at said each of the plurality of axial locations.

Clause 87. The method of any of clauses 45 to 86, wherein the treatment plan is configured to adjust one or more of an intensity of energy from the energy source, a power of energy from the energy source, a translation of the probe along the treatment probe axis, a rotation of the probe about the treatment probe axis, a translational velocity of the treatment probe, a rotational velocity of the treatment probe, or a number of passes of the energy source along the tissue, in order to treat the tissue to different depths in accordance with a treatment profile.

Clause 88. The method of any of clauses 45 to 87, wherein the treatment plan is configured to fix an axial position of the treatment probe and rotate the treatment probe at the axial position to scan energy from the energy source along the tissue with a first pass between first angles and a second pass between second angles at the axial position.

Clause 89. The method of any of clauses 45 to 88, wherein a first portion tissue between the first angles does not overlap with the second angles to treat tissue to a first depth with the first pass and wherein the second angles overlap with the first angles to treat tissue to a second depth with the first pass and the second pass.

Clause 90. The method of any of clauses 45 to 89, wherein the treatment plan is configured to fix a rotational angle of the treatment probe about the elongate probe axis and translate the treatment probe at the rotational angle to scan energy from the energy source along the tissue with a first pass between first translational locations and a second pass between second translational location at the rotational angle.

Clause 91. The method of any of clauses 45 to 90, wherein the treatment plan is configured to increase a translational velocity of the energy source on the treatment probe to decrease a treatment depth and decrease the translational velocity to increase the treatment depth.

Clause 92. The method of any of clauses 45 to 91, wherein the treatment plan is configured to increase a rotational velocity of the energy source on the treatment probe to decrease a treatment depth and decrease the rotational velocity to increase the treatment depth.

Clause 93. The method of any of clauses 45 to 92, wherein each of the plurality of transverse image comprises a second tissue and a boundary of the second tissue is determined and an output to a user interface generated in response to a location of the boundary of the second tissue.

Clause 94. The method of any of clauses 45 to 93, wherein the location of the second tissue boundary is between the first angle and the second angle and the output is generated in response to the location of the second tissue boundary between the first angle and the second angle.

Clause 95. The method of any of clauses 45 to 94, wherein the boundary of the first tissue is located between the boundary of the second tissue and the output is generated in response to a distance between the probe and the location of the second tissue boundary.

Clause 96. The method of any of clauses 45 to 95, wherein the treatment plan comprises an angle of rotation of an energy source beyond a margin of the boundary of the first tissue and the output is generated in response to the angle of rotation beyond the margin.

Clause 97. The method of any of clauses 45 to 96, wherein the treatment plan corresponds to a depth of penetration of an energy source beyond a thickness of the tissue and the output is generated in response to the depth of penetration greater than the thickness.

Clause 98. The method of any of clauses 45 to 97, wherein the thickness comprises a plurality of thicknesses at a plurality of rotation angles of an energy source and each of the plurality of thicknesses is determined for a corresponding angle of the plurality of rotation angles.

Clause 99. The method of any of clauses 45 to 98, wherein said each of the plurality of thicknesses comprises a distance between a first location of the first tissue boundary and a second location of the first tissue boundary at the corresponding angle and the depth of penetration is determined for said each of the plurality of thicknesses.

Clause 100. The method of any of clauses 45 to 99, wherein the output to the user interface comprises feedback to a user and optionally wherein the feedback comprises one or more of a notification or an alert.

Clause 101. The method of any of clauses 45 to 100, wherein the output to the user interface is configured for a user to adjust a treatment profile shown on one or more of the plurality of transverse images in response to the feedback.

Clause 102. The method of any of clauses 45 to 101, wherein the treatment profile substantially encloses the area, and the user interface is configured for the user to adjust the treatment profile with respect to the area by moving the treatment profile as shown on a display for each of the plurality of transverse images.

Clause 103. The method of any of clauses 45 to 102, wherein the user interface is configured for the user to adjust one or more of an angle of the treatment profile with respect to the probe or a depth of the treatment profile with respect to the probe.

Clause 104. The method of any of clauses 45 to 103, wherein the boundary of the first tissue, the boundary of the second tissue, and a treatment profile are shown on each of the plurality of transverse images and the user interface is configured to adjust the treatment profile on the plurality of transverse images.

Clause 105. The method of any of clauses 45 to 104, wherein the boundary of the first tissue and the boundary of the second tissue is determined with an AI algorithm.

Clause 106. The method of any of clauses 45 to 105, wherein the first tissue comprises a first anatomical tissue structure and the second tissue comprises a second anatomical tissue structure different from the first anatomical tissue structure.

Clause 107. The method of any of clauses 45 to 106, wherein the first anatomical tissue structure comprises an anatomical tissue structure of a first organ and the second anatomical tissue structure comprises a second anatomical tissue structure of a second organ different from the first organ.

Clause 108. The method of any of clauses 45 to 107, wherein the first anatomical tissue structure comprises one or more of an anatomical structure of the first tissue structure comprises one or more of a tissue wall, a vesicle, a lumen, a wall of a lumen, a bladder, a wall of a bladder, a neck of a bladder, a wall of a bladder neck, a ureteric orifice, an internal urethral orifice, an external urethral sphincter, a ureter, a wall of a ureter, a prostate, a lobe of a prostate, an intravesical prostatic protrusion, a capsule of a prostate, an internal sphincter, and external sphincter, an artery, a wall of an artery, a vein, a wall of a vein, or a lens of an eye, and the second anatomical tissue structure comprises one or more of wherein the anatomical structure of the second tissue structure comprises one or more of a tissue wall, a vesicle, a lumen, a wall of a lumen, a bladder, a wall of a bladder, a neck of a bladder, a wall of a bladder neck, a trigone tissue, a ureteric orifice, an internal urethral orifice, an external urethral sphincter, a ureter, a wall of a ureter, a prostate, a lobe of a prostate, an intravesical prostatic protrusion, a capsule of a prostate, a verumontanum of a prostate, an internal sphincter, and external sphincter, an artery, a wall of an artery, a vein, a wall of a vein, or a retina of an eye.

Clause 109. The method of any of clauses 45 to 108, wherein the first anatomical tissue structure comprises the intravesical prostatic protrusion of the prostate and the second anatomical tissue structure comprises the trigone of the bladder.

Clause 110. The method or apparatus of any one of the preceding clauses wherein treatment comprises one or more of ablation, resection, or irradiation of the tissue.

Clause 111. The method of any one of the preceding clauses, wherein the method comprises treating the patient.

Clause 112. An apparatus, comprising: a processor configured to perform the method of any one of the preceding clauses.

Clause 113. The method or apparatus of any one of the preceding clauses wherein the one or more longitudinal images comprises one or more of a sagittal image or a parasagittal image.

Clause 114. The method or apparatus of any one of the preceding clauses, wherein the plurality of transverse images extends transversely to the one or more longitudinal images and optionally perpendicularly to the one or more longitudinal images.

Clause 115. The method or apparatus of any one of the preceding clauses, wherein the plurality of transverse images and the one or more longitudinal images have been rotated to align the one or more longitudinal images with an elongate axis of a treatment probe.

Clause 116. The method or apparatus of any one of the preceding clauses, wherein the processor is configured with instructions to determine a 3D treatment profile of the tissue with an AI algorithm and to provide the 3D treatment profile on a display for a user to one or more of verify or adjust the 3D treatment profile.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A method of planning a treatment, the method comprising:
    receiving one or more longitudinal images of a tissue;
    generating an arrangement of a plurality of transverse images of the tissue along the one or more longitudinal images of the tissue in a three-dimensional (3D) view, the 3D view comprising the plurality of transverse images at a plurality corresponding locations along the one or more longitudinal images;
    overlaying a representation of a three-dimensional (3D) treatment profile on the 3D view of the plurality of transverse images and the one or more longitudinal images;
    providing, to a display of a user interface, the 3D view with the representation of the 3D treatment profile overlaid on the one or more longitudinal images and one or more of the plurality of transverse images; and
    determining, for each of the plurality of transverse images, one or more treatment angles from a treatment probe to one or more treatment locations;
    wherein the representation of the 3D treatment profile in the 3D view comprises an intersection of the 3D treatment profile with the one or more longitudinal images and one or more of the plurality of transverse images.

2. The method of claim 1, wherein in the 3D view, the plurality of transverse images comprises a first portion on a first side of the one or more longitudinal images and a second portion on a second side of the one or more longitudinal images, the first portion in front of the one or more longitudinal images and the second portion behind the one or more longitudinal images.

3. The method of claim 2, wherein the representation of the 3D treatment profile is overlaid in the 3D view on the first portion and the one or more longitudinal images, with the representation extending along the first portion and the one or more longitudinal images from a common location where the first portion intersects the one or more longitudinal images.

4. The method of claim 2, wherein the one or more longitudinal images comprises an amount of transparency sufficient to view the second portion of one or more transverse images through the one or more longitudinal images.

5. The method of claim 4, wherein the representation of the 3D treatment profile is overlaid on the second portion on the second side and the amount of transparency is sufficient to view the representation of the 3D treatment profile on the second side through the one or more longitudinal images.

6. The method of claim 1, wherein the arrangement comprises a three-dimensional (3D) arrangement and the user interface comprises an input for a user to one or more of zoom, pan or rotate the 3D arrangement in the 3D view.

7. The method of claim 6, wherein the representation of the 3D treatment profile moves with the 3D arrangement to maintain registration of the 3D treatment profile with the 3D arrangement in response to a user input to one or more of zoom, pan or rotate the representation.

8. The method of claim 7, wherein the user input is configured to rotate the one or more longitudinal images and the plurality of transverse images from a first orientation to a second orientation, the first orientation showing a first portion of the plurality of transverse images in front of the one or more longitudinal images and a second portion of the plurality of transverse images behind the one or more longitudinal images, the second orientation showing the second portion of the plurality of transverse images in front of the one or more longitudinal images and the second portion of one or more of the plurality of transverse images behind the one or more longitudinal images.

9. The method of claim 7, wherein a representation of a treatment probe is shown extending along the one or more longitudinal images and the representation of the treatment probe moves with the 3D arrangement and the 3D treatment profile to maintain registration of the representation of the treatment probe with the 3D arrangement and the 3D treatment profile.

10. The method of claim 1, wherein the representation of the 3D treatment profile comprises a three-dimensional (3D) treatment volume overlaid on the arrangement.

11. The method of claim 10, wherein the 3D treatment volume extends along the one or more longitudinal images in a longitudinal direction and along one or more of the plurality of transverse images in a direction transverse to the one or more longitudinal images.

12. The method of claim 11, wherein an outer boundary of the 3D treatment volume is shown extending along the one or more longitudinal images transverse to the one or more longitudinal images and along a transverse image in the longitudinal direction.

13. The method of claim 1, wherein a representation of a treatment probe is shown in the 3D view extending in a longitudinal direction.

14. The method of claim 13, wherein the representation of the treatment probe comprises an animation of the treatment probe.

15. The method of claim 14, wherein the animation of the treatment probe is configured to move to show an animation of the treatment probe delivering energy from an energy source in accordance with a treatment plan.

16. The method of claim 13, wherein the representation of the treatment probe comprises an image of the treatment probe from an imaging device.

17. The method of claim 1, wherein the plurality of transverse images corresponds to a plurality of predefined anatomical locations of an organ.

18. The method of claim 17, wherein the plurality of predefined anatomical locations comprises anatomical locations of first organ and a second organ in which the first organ and the second organ are visible in the one or more longitudinal images and one or more of the transverse images.

19. A method of planning a treatment, the method comprising:

receiving a plurality of transverse images and one or more longitudinal images of a tissue;

generating an arrangement of the plurality of transverse images along the one or more longitudinal images in a three-dimensional (3D) view, the 3D view comprising the plurality of transverse images at a plurality corresponding locations along the one or more longitudinal images;

overlaying a representation of a three-dimensional (3D) treatment profile on the 3D view of the plurality of transverse images and the one or more longitudinal images; and providing to a display of a user interface, the 3D view with the representation overlaid on the one or more longitudinal images and one or more of the plurality of transverse images;

wherein the plurality of transverse images corresponds to a plurality of predefined anatomical locations of an organ;

wherein the plurality of predefined anatomical locations comprises anatomical locations of first organ and a second organ in which the first organ and the second organ are visible in the one or more longitudinal images and one or more of transverse images; and wherein the plurality of predefined anatomical locations has been identified with an artificial intelligence algorithm.

* * * * *